United States Patent [19]

Sekino et al.

[11] Patent Number: 5,273,027
[45] Date of Patent: Dec. 28, 1993

[54] METHOD FOR DISSOLVING A THICKENED MASS WITHIN A LIVING BODY AND DISSOLVING THERAPEUTIC APPARATUS FOR SAME

[75] Inventors: Naomi Sekino; Koji Fujio; Koichiro Ishiwara; Naoki Uchiyama; Kenji Noda; Seiji Iwasaki; Shuichi Takayama; Tsuyoshi Tsukagoshi; Koji Koda, all of Tokyo, Japan

[73] Assignee: Olympus Optical Co., Ltd., Tokyo, Japan

[21] Appl. No.: 589,945

[22] Filed: Sep. 28, 1990

[30] Foreign Application Priority Data

| Mar. 27, 1990 | [JP] | Japan | 2-32660[U] |
| Mar. 27, 1990 | [JP] | Japan | 2-80448 |
| Mar. 27, 1990 | [JP] | Japan | 2-80449 |
| Mar. 27, 1990 | [JP] | Japan | 2-80450 |
| Mar. 27, 1990 | [JP] | Japan | 2-80451 |
| May 17, 1990 | [JP] | Japan | 2-129834 |
| May 18, 1990 | [JP] | Japan | 2-128889 |
| Jul. 23, 1990 | [JP] | Japan | 2-196728 |

[51] Int. Cl.⁵ .......... A61B 17/00; A61B 8/00
[52] U.S. Cl. ............ 128/24 A; 128/660.03; 604/49; 604/28; 604/31; 604/67
[58] Field of Search ............ 128/DIG. 12, 13, 27, 128/30, 31, 24 A, 660.03; 604/22, 28, 48, 49–54, 65–66; 606/127, 128

[56] References Cited

U.S. PATENT DOCUMENTS

| 4,464,172 | 8/1984 | Lichtenstein | 128/DIG. 13 X |
| 4,655,744 | 4/1987 | Thistle et al. | 604/28 |
| 4,755,167 | 7/1988 | Thistle et al. | 604/28 |
| 4,902,276 | 2/1990 | Zakko | 604/28 |
| 4,994,025 | 2/1991 | DeAntonio et al. | 604/27 X |
| 5,018,508 | 5/1991 | Fry et al. | 128/24 AA |
| 5,098,377 | 3/1992 | Barsanyi et al. | 604/30 |

Primary Examiner—Francis Jaworski
Attorney, Agent, or Firm—Armstrong, Westerman, Hattori, McLeland & Naughton

[57] ABSTRACT

In the method and dissolving therapeutic apparatus for dissolving a coagulation within a living body, a medicinal liquid for dissolving the coagulation within the living body is injected into the living body, the injected medicinal liquid is left within the living body for a predetermined time and the fluid within the living body containing the coagulation dissolved by the medicinal liquid and the medicinal liquid is substantially all discharged out of the living body. A series of steps including at least respective injecting, leaving and discharging steps is repeated. Preferably, vibrating waves are radiated toward the coagulation during the leaving step.

41 Claims, 21 Drawing Sheets

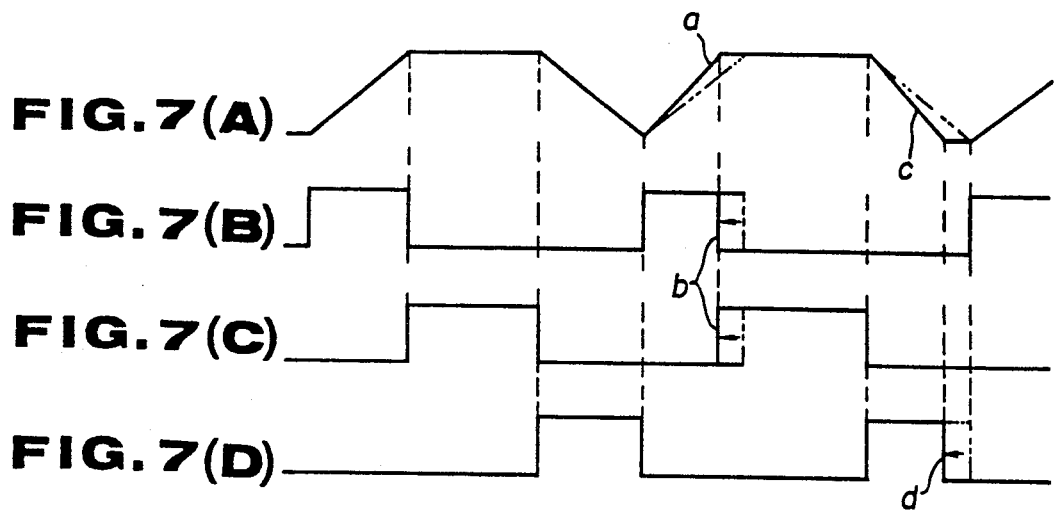
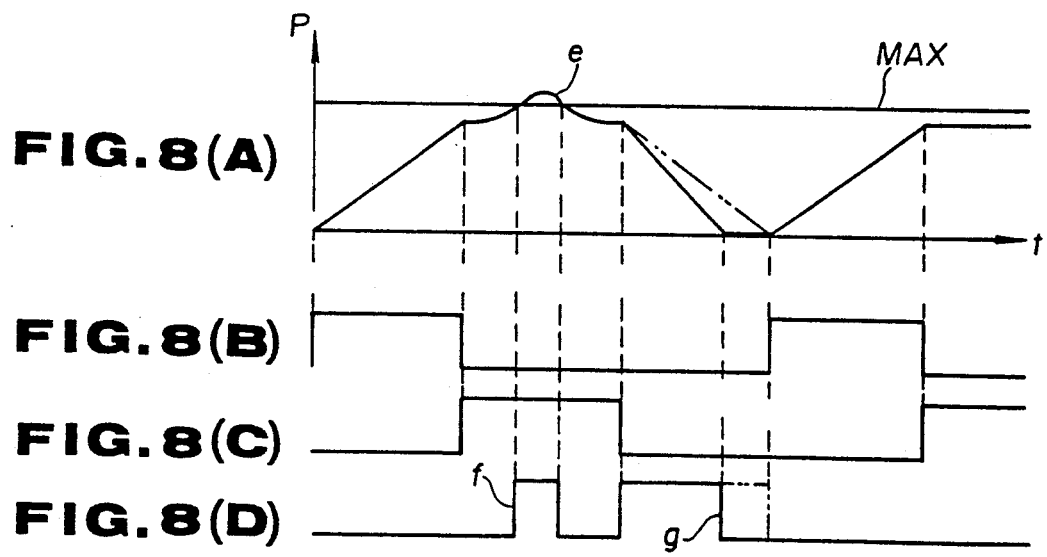

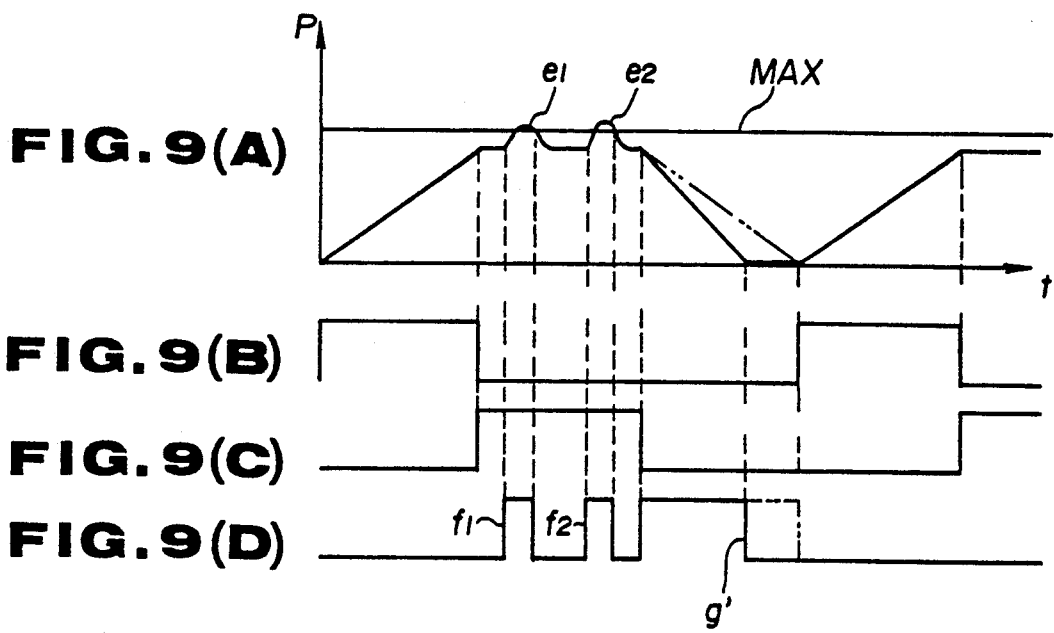
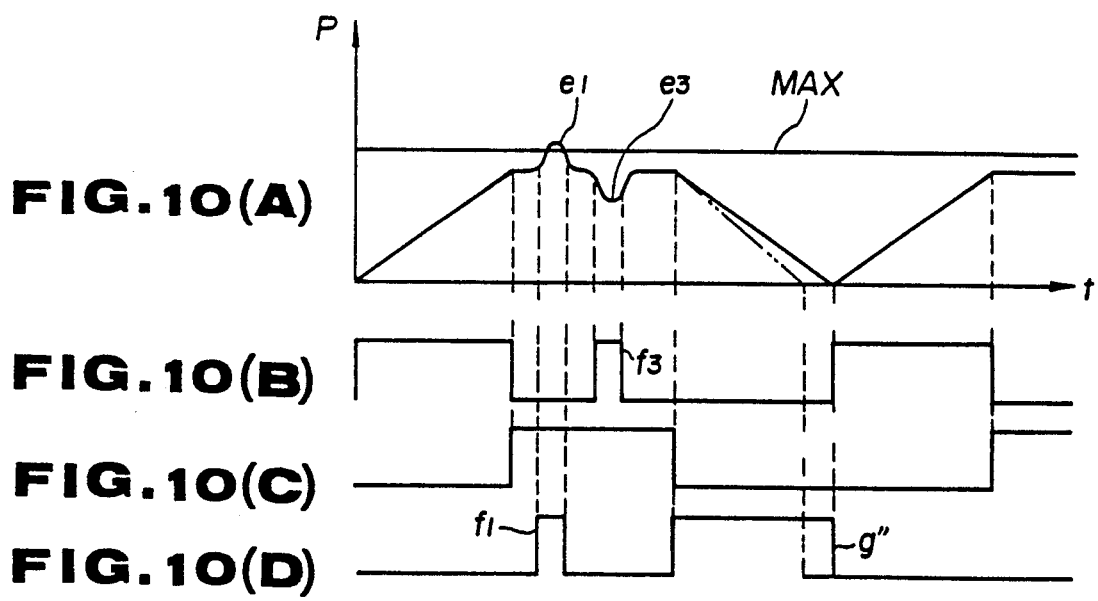

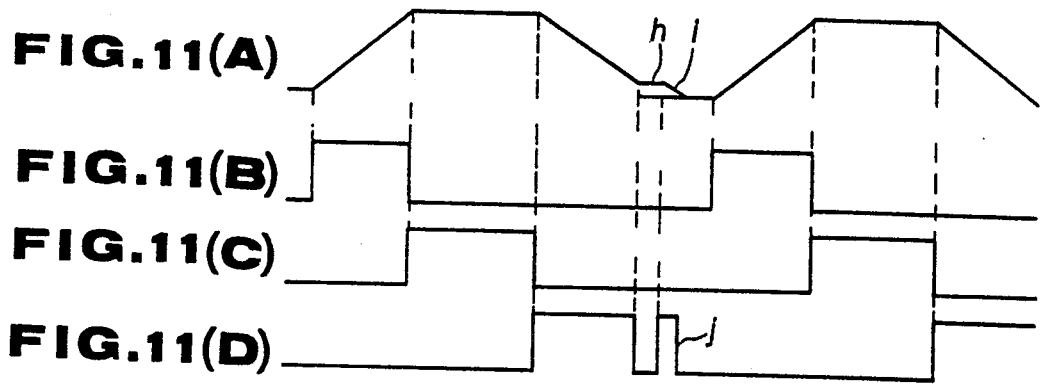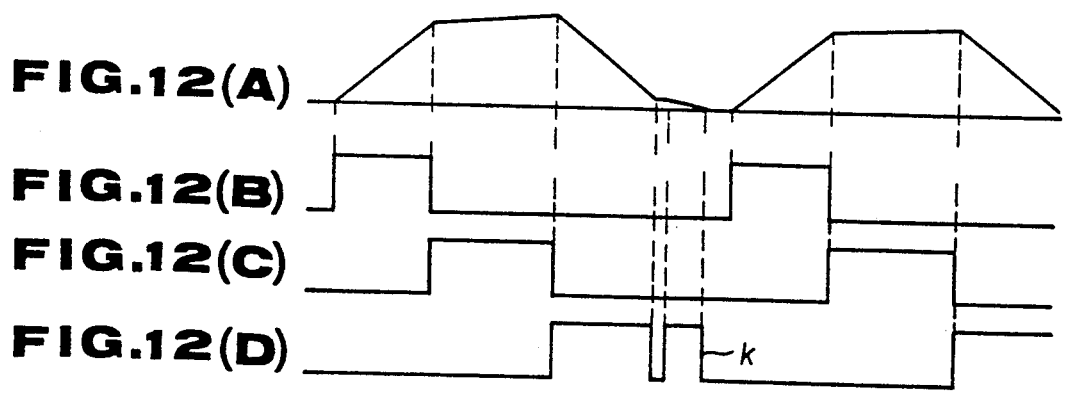

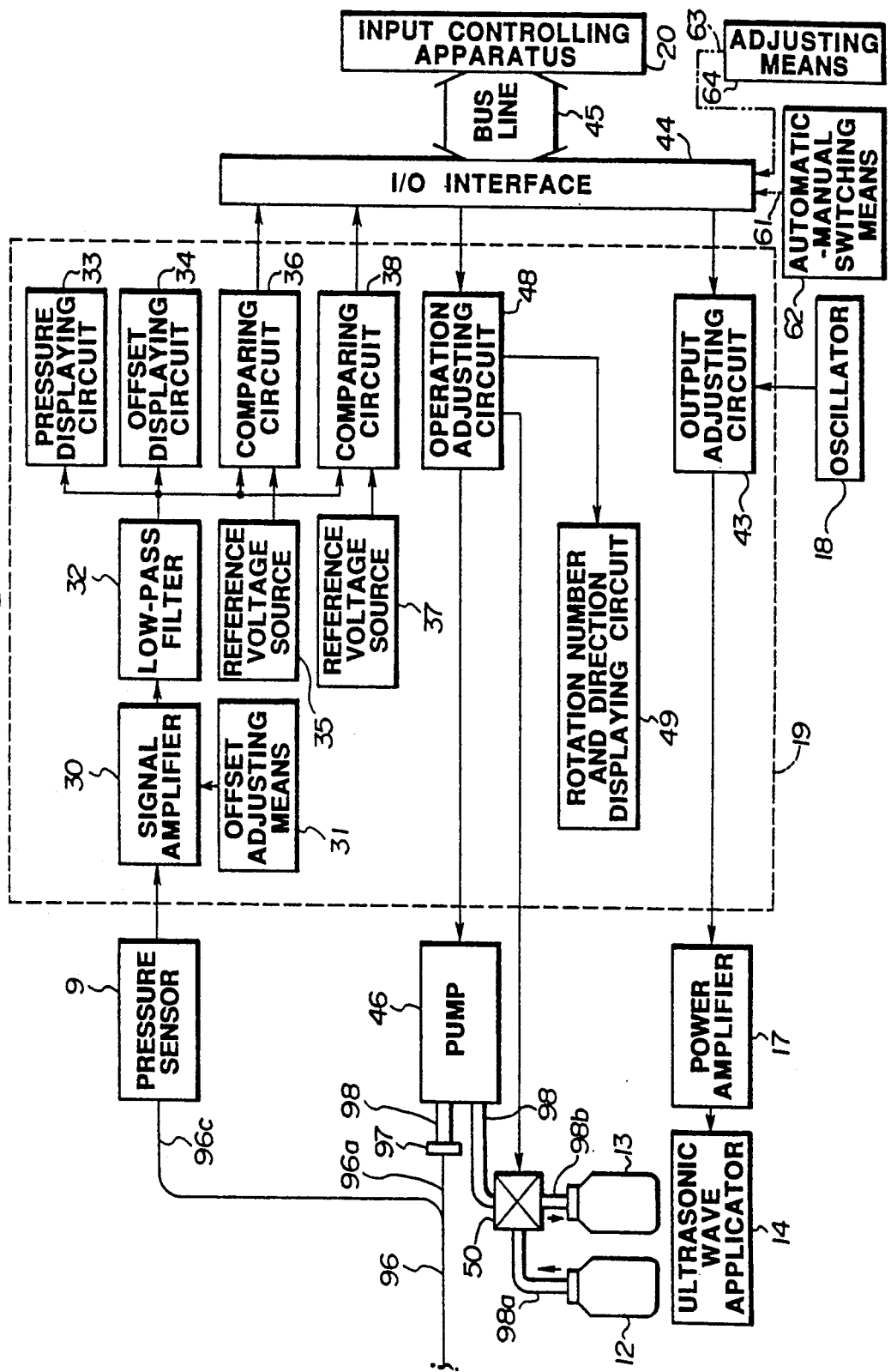

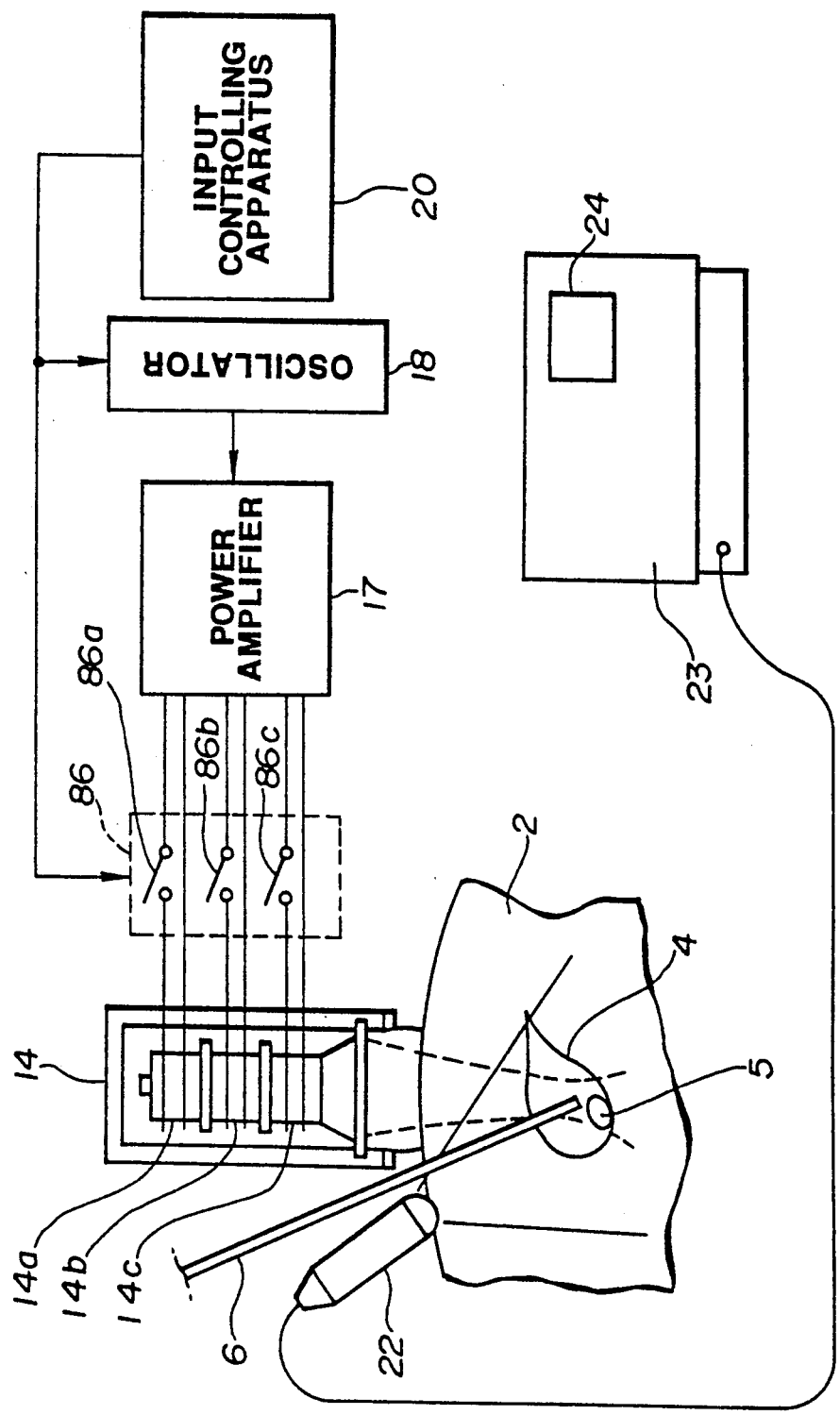

METHOD FOR DISSOLVING A THICKENED MASS WITHIN A LIVING BODY AND DISSOLVING THERAPEUTIC APPARATUS FOR SAME

BACKGROUND OF THE INVENTION

1. Field of the Invention

This, invention relates to a method for dissolving a thickened mass within a living body by introducing a medicinal liquid dissolving a thickened mass within a living body or accelerating and helping such dissolution around the thickened mass within the living body and recovering out of the body the fluid containing the dissolved component of the thickened mass and to a dissolving therapeutic apparatus for the same. The term "thickened mass" is understood to include both a "calculous" and a "thrombus".

2. Description of the Related Art

There is already considered a dissolving therapeutic apparatus wherein a medicinal liquid which is of such stone dissolving agent as monooctanoin, d-limonene or methyl t-butyl ether (MTBE) is injected into such treated part as the gallbladder within a living body and is left for a fixed time so that such thickened mass as a stone present in the treated part may be dissolved by said medicinal liquid and such fluid as the medicinal liquid in which this thickened mass is dissolved is sucked to remove said stone or the like.

Some means for improving the coagulation dissolving efficiency to be higher than ever are suggested in said dissolving therapeutic apparatus. In the publications, for example, of U.S. Pat. No. 4,655,744 and Japanese Patent Application Laid Open No.117545/1987 is suggested an apparatus wherein a fixed amount of a medicinal liquid is injected and sucked into such treated part as the gallbladder within a living body by using a pump and is stirred so as to accelerate the dissolution of the thickened mass.

Also, in the publications of U.S. Pat. No. 4,902,276 and Japanese Patent Application Laid Open No.40541/1988 is suggested an apparatus wherein a fluid (medicinal liquid) is simultaneously injected and sucked and is refluxed. The apparatus shown in the publications is provided also with a means for controlling the injection and suction of the medicinal liquid so as to hold the pressure within the gallbladder to be within a set range.

However, in the apparatus shown in said publications of U.S. Pat. No. 4,655,744 and Japanese Patent Application Laid Open No.11754/1987, the injection and suction of the medicinal liquid for dissolving the thickened mass are repeated to stir the liquid but a new medicinal liquid is not always introduced into the treated part. In said apparatus, a trap for passing the fluid sucked from the therapeutic part is provided and Yet the cholesterol component dissolved in the medicinal liquid gradually increases, the dissolving efficiency reduces and the dissolving time becomes long.

In the apparatus shown in said publications of U.S. Pat. No. 4,902,276 and Japanese Patent Application Laid Open No.40541/1988, the medicinal solution is refluxed to the therapeutic part but, the same as in the apparatus shown in the above described publications of U.S. Pat. No. 4,655,744 and Japanese Patent Application Laid Open No.117545/1987, the same medicinal liquid is repeatedly used and therefore there is a problem that the dissolving efficiency gradually reduces.

In both of said two examples, the medicinal liquid is always moved by the pump and is very likely to flow to parts other than the treated part.

In order to safely make the therapy by using the dissolving therapeutic apparatus, it is necessary to keep the pressure in the treated part lest the medicinal liquid should leak out of the treated part. A body liquid or the like often flows into said treated part and the pressure thereby must be also considered. Further, the pressure in the treated part may fluctuate due to the fine movement of the living body under the treatment. From these facts, the medicinal liquid is likely to flow out of the treated part.

SUMMARY OF THE INVENTION

An object of the present invention is to provide a method for dissolving a thickened mass within a living body wherein the efficiency of dissolving a thickened mass produced within a living body is high, the operations of injecting and sucking such fluid as a medicinal liquid are few and a dissolving therapeutic apparatus for the same.

Another object of the present invention is to provide a method for dissolving a thickened mass within a living body wherein a safe therapy can be made in addition to said object and a dissolving therapeutic apparatus for the same.

A further object of the present invention is to provide a method for dissolving a thickened mass within a living body wherein the dissolution can be accelerated without making injecting and sucking operations in addition to said first object and a dissolving therapeutic apparatus for the same.

A further object of the present invention is to provide a dissolving therapeutic apparatus wherein a vibrating wave for accelerating the dissolution of a coagulation can be radiated in an accurate position relation with the coagulation.

In the method for dissolving a coagulation within a living body and the dissolving therapeutic apparatus for the same of the present invention, a medicinal liquid for dissolving a coagulation within a living body is injected into the living body and is left for a predetermined time within the living body, substantially all the fluid within the living body containing the coagulation dissolved by the medicinal liquid and the medicinal liquid is discharged out of the living body, a series of steps including at least said respective injecting, leaving and discharging steps are repeated and preferably a vibrating wave is radiated toward the coagulation in said leaving step.

In the present invention, a series of at least the injecting, leaving and sucking steps are repeated. In considering the time when the medicinal liquid dissolves the coagulation, even if the medicinal liquid is left for any time, the dissolving effect will not be reduced. Therefore, in the present invention, in considering the dissolving capacity of the medicinal liquid, after the medicinal liquid is injected, while the medicinal liquid has a sufficient dissolving effect, that is, while the thickened mass dissolved in the medicinal liquid is not saturated, the medicinal liquid is not put out of or into the body. Before the medicinal liquid becomes unable to dissolve, that is, before the thickened mass dissolved in the medicinal liquid is saturated, the medicinal liquid within the living body is replaced with a new medicinal liquid.

By the way, it is desirable that this medicinal liquid is slowly replaced. Thus, according to the present invention, with the movement of little medicinal liquid, the thickened mass dissolving therapy can be effectively made and is safe.

In the dissolving therapeutic apparatus of the present invention, preferably, a pressure detecting means for detecting the pressure of the medicinal liquid injecting part is provided, usually the respective steps are controlled according to a time table and, when said pressure detecting means detects that the pressure of the injecting part has exceeded a predetermined pressure, said pressure will be adjusted so as to be below said predetermined pressure.

The dissolving therapeutic apparatus of the present invention comprises an ultrasonic observing apparatus for observing an ultrasonic image of an observed part within a living body, a vibrating wave generating apparatus for applying a vibrating wave for accelerating the dissolution of the coagulation to the treated part within the living body and supporting apparatus for supporting said ultrasonic observing apparatus and said vibrating wave generating apparatus. The supporting apparatus includes a moving means for moving said observing apparatus and said vibrating wave generating apparatus so as to selectively arrange the observed part of said observing apparatus and the treated part of said vibrating wave generating apparatus in any desired part of the living body.

BRIEF DESCRIPTION OF THE DRAWINGS

FIGS. 1 to 9 relate to the first embodiment of the present invention.

FIG. 1 is a block diagram showing the formation of a dissolving therapeutic apparatus.

FIG. 2 is an explanatory view showing the formation of the whole of the dissolving therapeutic apparatus.

FIG. 4 is an explanatory view showing a parameter change by a pressure control.

FIG. 5 is an explanatory view showing the sequence of the dissolving therapeutic apparatus.

FIG. 6 is an explanatory view showing an example of displaying the therapeutic contents at the time of a therapeutic operation.

FIGS. 7(A) to (D) are explanatory views showing a first operation example of a dissolving therapeutic apparatus.

FIGS. 8(A) to (D) are explanatory views showing a second operation example of a dissolving therapeutic apparatus.

FIGS. 9(A) to (D) are explanatory views showing a third operation example of a dissolving therapeutic apparatus.

FIG. 10 is an explanatory view showing a sequence of the dissolving therapeutic apparatus of the second embodiment of the present invention.

FIGS. 11 and 12 are explanatory views each showing a sequence of the dissolving therapeutic apparatus of the third embodiment of the present invention.

FIG. 13 is a block diagram showing the formation of a dissolving therapeutic apparatus of the fourth embodiment of the present invention.

FIGS. 14 and 15 relate to the fifth embodiment of the present invention.

FIG. 14 is an explanatory view showing a control system of an ultrasonic applicator.

FIGS. 15 is a characteristic diagram showing the relation between the dissolving time and the size of the gallstone.

FIG. 16 is a sectioned view of an ultrasonic applicator.

FIG. 17 is a disassembled view of an ultrasonic applicator.

FIG. 18 is a sectioned view showing an ultrasonic applicator and ultrasonic probe.

FIG. 19 is a sectioned view on line A—A' in FIG. 18.

FIG. 20 is a sectioned view showing an ultrasonic applicator and ultrasonic probe.

FIG. 21 is a sectioned view on line C—C' in FIG. 20.

FIG. 24 is an explanatory view showing a schematic formation of a dissolving therapeutic apparatus.

FIG. 25 is a sectioned view of an essential part of an ultrasonic applicator.

FIGS. 1 to 9 show the first embodiment of the present invention.

DESCRIPTION OF THE PREFERRED EMBODIMENTS

Figure 2:
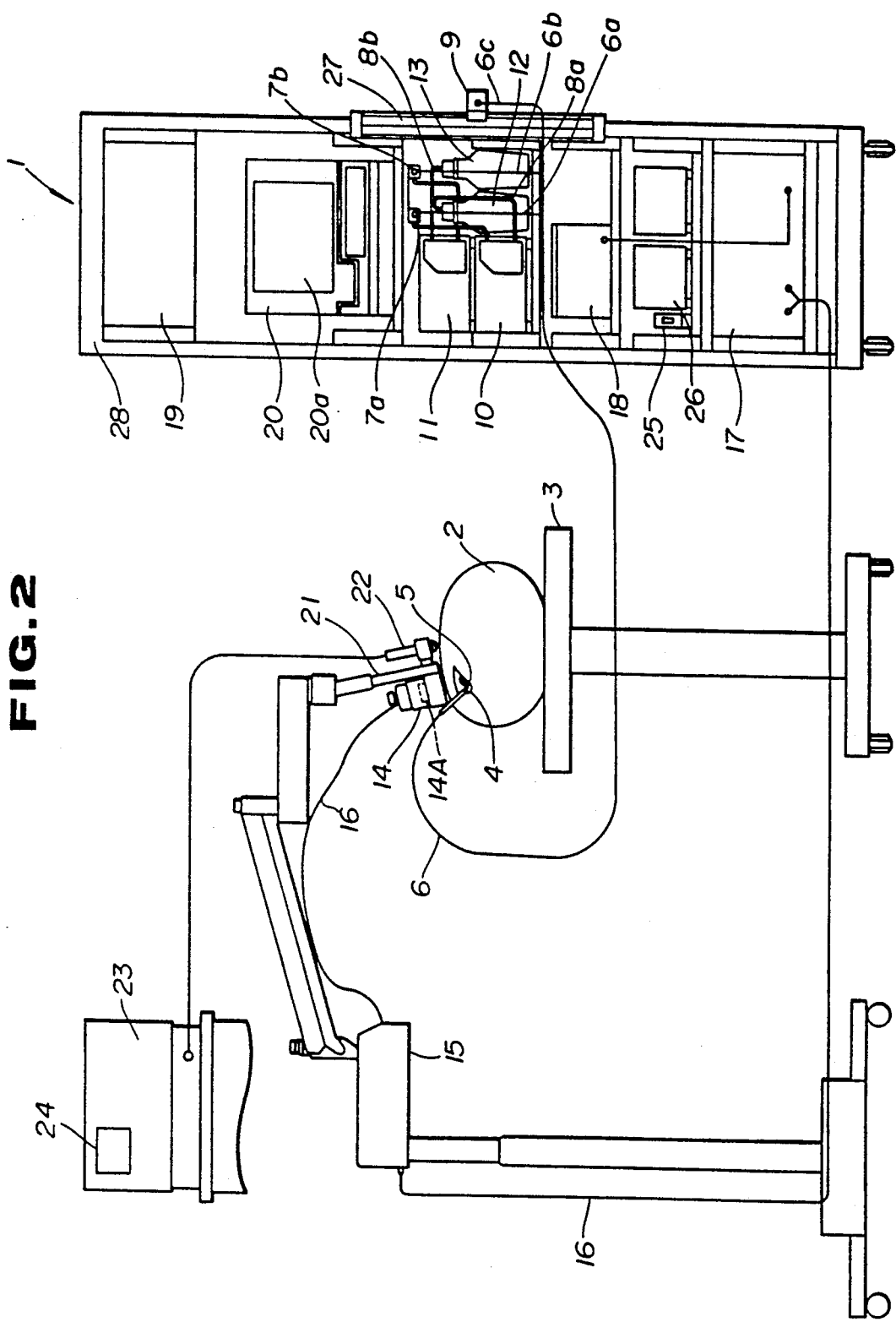

As shown in FIG. 2, a human body 2 to be treated by a dissolving therapeutic apparatus 1 is mounted on a treating stand and a stone 5 is produced, for example, in a gallbladder 4 which is a treated part within said human body 2.

The dissolving therapeutic apparatus 1 is provided with a catheter 6 which is dermally inserted at the tip into said gallbladder 4. This catheter 6 is formed of a porous tube and has three lumina of an injection pipe line 6a, suction pipe line 6b and pressure pipe line 6c. The above described three lumina of said catheter 6 are branched at the rear end of the catheter, the injection pipe line 6a is connected to an injection pump tube 8a through a connector 7a, the suction pipe line 6b is connected to a suction pump tube 8b through a connector 7b and the pressure pipe line 6c is connected to a pressure sensor 9.

The injection pump tube 8a has an injection pump 10 interposed in the intermediate part and is connected at the end to a liquid tank 12 storing a medicinal liquid which is a stone dissolving agent, for example, by monooctanoin, d-limonene or methyl t-butyl ether (MTBE).

The suction pump tube 8b has a suction pump 11 interposed in the intermediate part and is connected at the end to a discharged liquid tank 13 storing the fluid recovered from the treated part.

Further, the injection pump 10 and suction pump 11 are connected to an inputting and controlling apparatus 20 through a controlling unit 19 so that the pump rotation number may be freely set by the controlling unit 19, the driving time and switching operation of the respective pumps may be set by the input controlling apparatus 20 and the pump may operate in response to the set contents. Said inputting and controlling apparatus 20 has a displaying part 20a.

Also, an ultrasonic applicator 14 radiating ultrasonic waves as vibrating waves to said gallbladder 4 which is the above described treated part is provided as a vibrating wave generating means, has one or more ultrasonic vibrators 14 within it, is supported and fixed by a supporting member 21 arranged in the tip part of the supporting arm 15 and is connected to a power amplifier 17 by a cable 16.

A later described output signal of an oscillator 18 is to be input into said power amplifier 17.

A signal adjusted and set in the frequency, amplitude, pulse number, pulse interval and driving time of the output signal is to be input into the oscillator 18 from the controlling unit 19. The output signal of this oscillator 18 is amplified by the power amplifier 17 and this amplified signal is applied to an ultrasonic vibrator 14A within said ultrasonic applicator.

Ultrasonic waves excited by said ultrasonic vibrator 14A are to be radiated to the vicinity including the gallstone 5 present within said gallbladder 4 of said human body 2.

An observing ultrasonic probe 22 is removably held on the side opposite the ultrasonic applicator 14 with the center axis of the supporting member 21 between them. Further, when the ultrasonic probe 22 and said applicator 14 are rotated by 180 degrees with the supporting member 21 in the center, the observing range center axis or the ultrasonic probe 22 and the ultrasonic wave radiating region center axis of the ultrasonic applicator 14 will coincide with each other.

The ultrasonic probe 22 is connected to the ultrasonic observing apparatus 23 so that an ultrasonic image including said gallbladder 4 within said human body 2 may be displayed in a monitor 24.

The controlling unit 19, inputting and controlling apparatus 20, injection pump 10, suction pump 11, oscillator 18 and power amplifier 17 are connected to a power source through an insulated transformer 26 and power source switch 25.

The pressure sensor 9 is movable in the vertical direction on a rail 27 and can be fixed in any position on the rail 27.

The controlling unit 19, input and control apparatus 20, connectors 7a and 7b, injection pump 10, suction pump 11, liquid tank 12, discharged liquid tank 13, oscillator 18, power source switch 25, insulated transformer 26, rail 27 and power amplifier 17 are set or fixed on a body rack 28.

Figure 1:
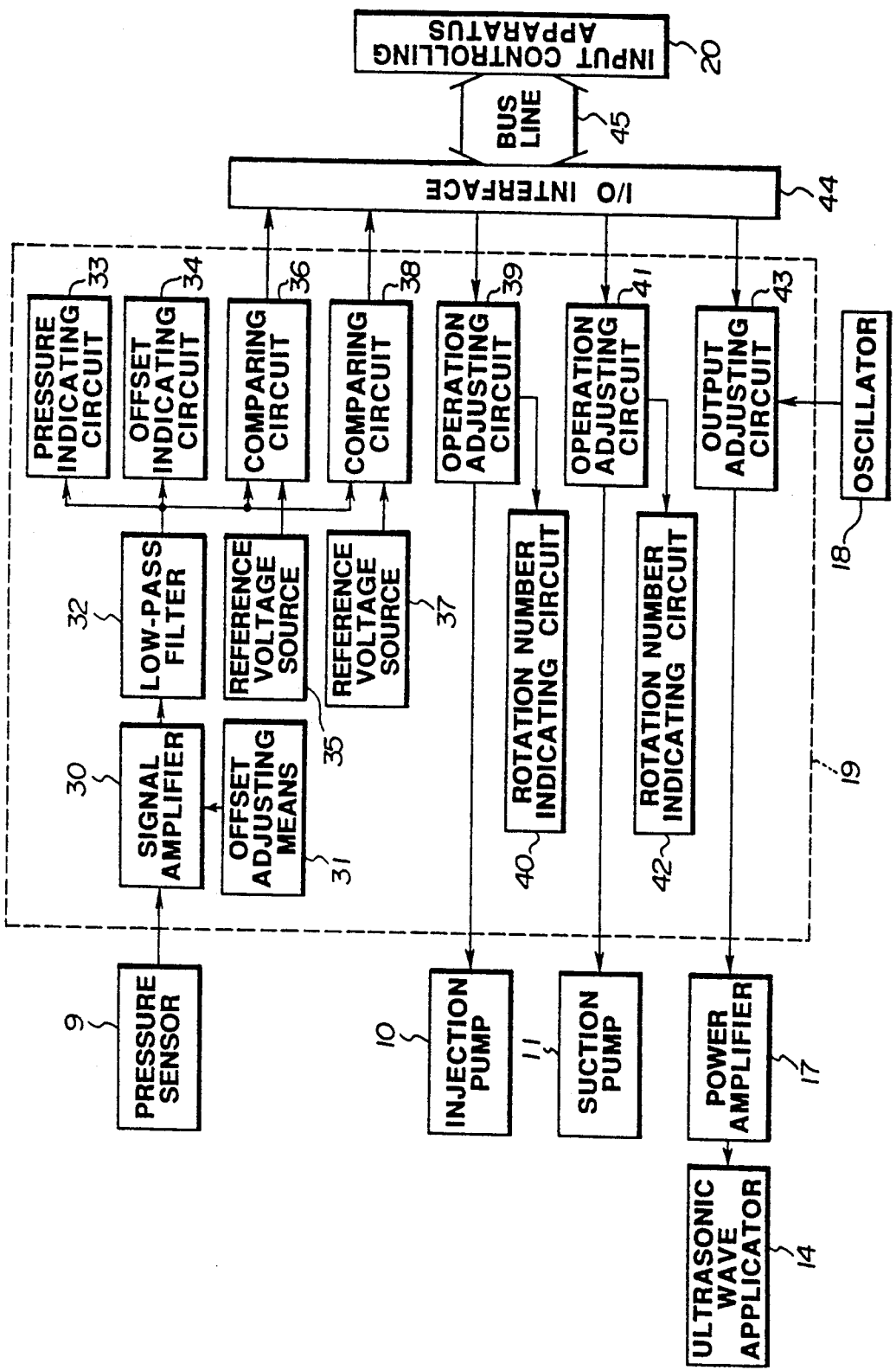

The formation relating to the controlling unit 19 shall be explained by using FIG. 1.

The pressure sensor 9 is connected to one input end of each of comparing circuits 36 and 38, a pressure displaying circuit 33 displaying the offset-adjusated pressure of the treated part or the like and an offset pressure displaying circuit (mentioned as an offset displaying circuit hereinafter) 34 used for the offset adjustment through a signal amplifier 30 and a low-pass filter 32. Further, an offset adjusting means 31 by a helical potentiometer or the like is connected to the signal amplifier 30.

A pressure signal of a detected pressure by the pressure sensor 9 is amplified in said signal amplifier 30, is corrected by an offset signal which is a correcting amount from said offset adjusting means 31 and is input into one input end of each of the comparing circuits 36 and 38, the pressure displaying circuit 33 and the offset displaying circuit 34 through said low-pass filter 32.

In the comparing circuit 36, said low-pass filter 32 is connected to one input end as described above, a reference voltage source 35 is connected to the other input end and the output end is connected to the input end of an I/O interface 44.

In the comparing circuit 38, said low-pass filter 32 is connected to one input end as described above, a reference voltage source 37 is connected to the other input end and the output end is connected to the input end of said I/O interface 44.

The I/O interface 44 is connected to the inputting and controlling apparatus 20 through a bus line 45.

The comparing circuit 36 compares the pressure signal corrected as described above and the reference voltage of the reference voltage source 35 with each other and outputs the signal of this compared result to the inputting and controlling apparatus 20 through the I/O interface 44 and bus line 45.

Further, the pressure signal corrected as described above is input into said pressure displaying circuit 33 and offset displaying circuit 34. Therefore, a value to which is added the attenuating characteristic by the low-pass filter 32 will be displayed by the pressure displaying circuit 33 and offset displaying circuit 34.

The input ends of said injection pump 10 and suction pump 11 are connected respectively to the output ends of operation adjusting circuits 39 and 41 whose input ends are connected to the output ends of the I/O interface 44.

Further, rotation number displaying circuits 40 and 42 are connected respectively to the operation adjusting circuits 39 and 41.

The output end of said oscillator 18 is connected to the input end of an output adjusting circuit 43.

In the output adjusting circuit 43, the input end is connected to said oscillator 18 as described above, the control end is connected to the output end of said I/O interface 44 and the output end is connected to the input end of said power amplifier 17.

The output end of the power amplifier 17 is connected to the ultrasonic applicator 14.

The signal from the oscillator 18 is input into the output adjusting circuit 43, is adjusted therein, for example, in respect of the frequency, amplitude, pulse number, pulse interval and driving time by the control signal of the input controlling apparatus 20 through the I/O interface 44 and bus line 45 and is then amplified in said power amplifier 17 to drive an ultrasonic vibrator not illustrated within the ultrasonic applicator 14.

Said I/O interface 44 has the input ends connected to the output ends of the comparing circuits 36 and 38 as described above, the output ends connected to the input ends of the operation adjusting circuits 39 and 41 and output adjusting circuit 43 as described above and the input and output end, for example, by a parallel signal connected to the input controlling apparatus 20 through the bus line 45.

The controlling unit 19 is formed of the signal amplifier 30, offset adjusting means 31, low-pass filter 32, pressure displaying circuit 33, offset displaying circuit 34, reference voltage sources 35 and 37, comparing circuits 36 and 38, operation adjusting circuits 39 and 41, rotation number displaying circuits 40 and 42 and output adjusting circuit 43.

The inputting and controlling apparatus 20 inputs from and controls the respective parts of said controlling unit 19 through the bus line 45 and I/O interface 44.

The operation of the thus formed dissolving therapeutic apparatus 1 shall be explained.

The power source switch 25 is switched on to start the dissolving therapeutic apparatus 1, then the liquid tank 12 is filled with a medicinal liquid and the injection pump 10 is rotated to remove air within the injection pipe line 6a.

Then, the supporting member 21 at the tip of the arm 15 is operated, the observing ultrasonic probe 22 is contacted at the tip with the human body 2 and the treated part, for example, the gallbladder 4 within the human body and the coagulation, for example, the stone 5 produced in the gallbladder 4 are probed. Here, the position of the ultrasonic probe 22 is adjusted so that the image of the stone 5 may be positioned on the center axis of the observed picture displayed in the monitor 24 of the ultrasonic observing apparatus 23. Further, the arm 15 and supporting member 21 are fixed in such positions as are described above.

Then, the distance from the body surface of said human body to the stone 5 is read and taken by the observed picture displayed in said monitor 24. Said pressure sensor 9 is moved on the rail 27 so that the position in the vertical direction of the pressure sensor 9 outside the body may substantially coincide with the position of the stone 5, that is, the treated part and is fixed in the substantially coinciding position.

Then, with the catheter 6 opened at the tip in the atmosphere, the initial pressure offset is adjusted by using the offset adjusting means 31 and offset displaying circuit 34 within the controlling unit 19.

The concrete adjusting method by the offset adjusting means 31 is that the offset signal is added from the offset adjusting means 31 to the signal from the pressure sensor 9 by said signal amplifier 30 and the signal is amplified or the amplifying degree of the signal amplifier 30 may be varied by the offset signal from the offset adjusting means 31.

Then, the catheter 6 is inserted at the tip into the gallbladder 4 within the body and the ultrasonic applicator 14 is rotated by 180 degrees with the center axis of the supporting member 21 as a rotation center and is set on the body surface.

Then, the suction pump 11 is rotated to discharge the bile. When the pressure within the gallbladder begins to become negative, the discharge of the bile is considered to end and the suction pump 11 is stopped.

Then, by the offset adjusting means 31, the pressure by the medicinal liquid or the like in the gallbladder 4 is adjusted to be zero. In this case, the pressure within the gallbladder 4 is displayed to be zero by the pressure displaying circuit 33. The indicated value of the minute positive pressure or negative pressure near this zero is displayed by the offset displaying circuit 34. Therefore, on the basis of the indicated value of the offset displaying circuit 34, the pressure within the gallbladder 4 detected by the pressure sensor 9 is offset-adjusted by the offset adjusting means 31 so as to be electrically zero.

Then, from the size of the gallbladder 4 and the kind and size of the stone 5 caught by the observed picture displayed in the monitor 24, the operator sets such therapeutic data as the numbers of rotations of the injection pump 10 and suction pump 11, the intensity of the radiated ultrasonic waves, the upper limit of the pressure by the medicinal liquid or the like within said gallbladder 4 and the responding speed of the pressure sensor 9 by the input part of the controlling unit 19 not illustrated. The above described therapeutic data are input into the inputting and controlling apparatus 20 through the bus line 45.

The inputting and controlling apparatus 20 sets a time sequence formed of the medicinal liquid injecting time, the therapeutic ultrasonic wave radiating time and the sucking time of the fluid sucked from the gallbladder 4, determines the number of repetitions of the sequence and is thereby set to control the operation adjusting circuits 39 and 41 and output adjusting circuit 43. The injection and suction speeds (flow volumes) are constant. The above described medicinal liquid injecting time represents in other words the amount of the injected medicinal liquid.

Then, on the basis of the setting, the therapy by the dissolving therapeutic apparatus 1 is started. When the dissolving therapeutic apparatus 1 stops, the observing ultrasonic probe 22 is rotated by 180 degrees with the center axis of the supporting member 21 as an object and whether the stone 5 within said gallbladder 4 has been dissolved or not is confirmed. Here, in case the stone 5 is still present, the ultrasonic applicator 14 is again set o the body surface of the human body 2 and the above described operation is repeated.

In case the stone 5 is confirmed to have been perfectly dissolved, the arm 15 is operated to remove the ultrasonic probe 22 or the ultrasonic applicator 14 from the human body 2. The catheter 6 is pulled off and the therapy ends.

Now, in the dissolving therapy, the reason why the injection of the medicinal liquid, radiation of ultrasonic waves and suction- and discharge of the medicinal liquid are repeated for a fixed time is as follows:

The amount of the medicinal soluation which can be injected into the gallbladder is about several cc. On the other hand, the dissolving degree, for example, of MTBE, that is, the amount of the gallstone which can be dissolved by 1 g. of MTBE is about 200 mg. Therefore, in order to dissolve, for example, 1 g. of the gallstone, at least 5 g. = 6.7 cc. of MTBE are required. If the injected amount of the dissolving agent is below 6.7 cc., the liquid will be saturated and will not be able to perfectly dissolve the gallstone. Therefore, if 4 cc. of the dissolving agent are injected each time, MTBE will have to be replaced at least twice. In the same manner, if the gallstone is 3 g., 15 g. = 20 cc. of MTBE will be required. If 4 cc./time are injected, MTBE will have to be replaced 5 or more times.

In the above explanation, the amount of the dissolving agent is a minimum amount based on the dissolving degree of MTBE. Therefore, in fact, an amount, for example, about 3 times as large is used. For example, if 60 cc. of the dissolving agent are to be used, MTBE will have to be replaced 15 times by 4 cc./time.

As in the above, from the dissolving degree of such dissolving agent as MTBE, the amount of the dissolving agent required for the perfect dissolution will be determined in response to the size of the gallstone. However, this amount is larger than the amount which can be generally safely injected into the gallbladder. Therefore, by replacing the dissolving agent at intervals of a fixed time, the gallstone can be perfectly dissolved.

In consideration of the dissolving capacity of the medicinal liquid, after the medicinal liquid is injected, while the medicinal liquid retains a sufficient dissolving effect, that is, while the dissolved coagulation in the medicinal liquid is not saturated, even if the medicinal liquid is not put out of and into the body, the dissolving efficiency will not reduce. Before the medicinal liquid becomes unable to dissolve the coagulation, that is, before the dissolved coagulation in the medicinal solution is saturated, the medicinal liquid within the living body is replaced with a fresh medicinal solution. Therefore, the time for leaving the medicinal liquid within the living body is set on the basis of such dissolving conditions as the size of the coagulation and the kind of the medicinal liquid.

Figure 3A:
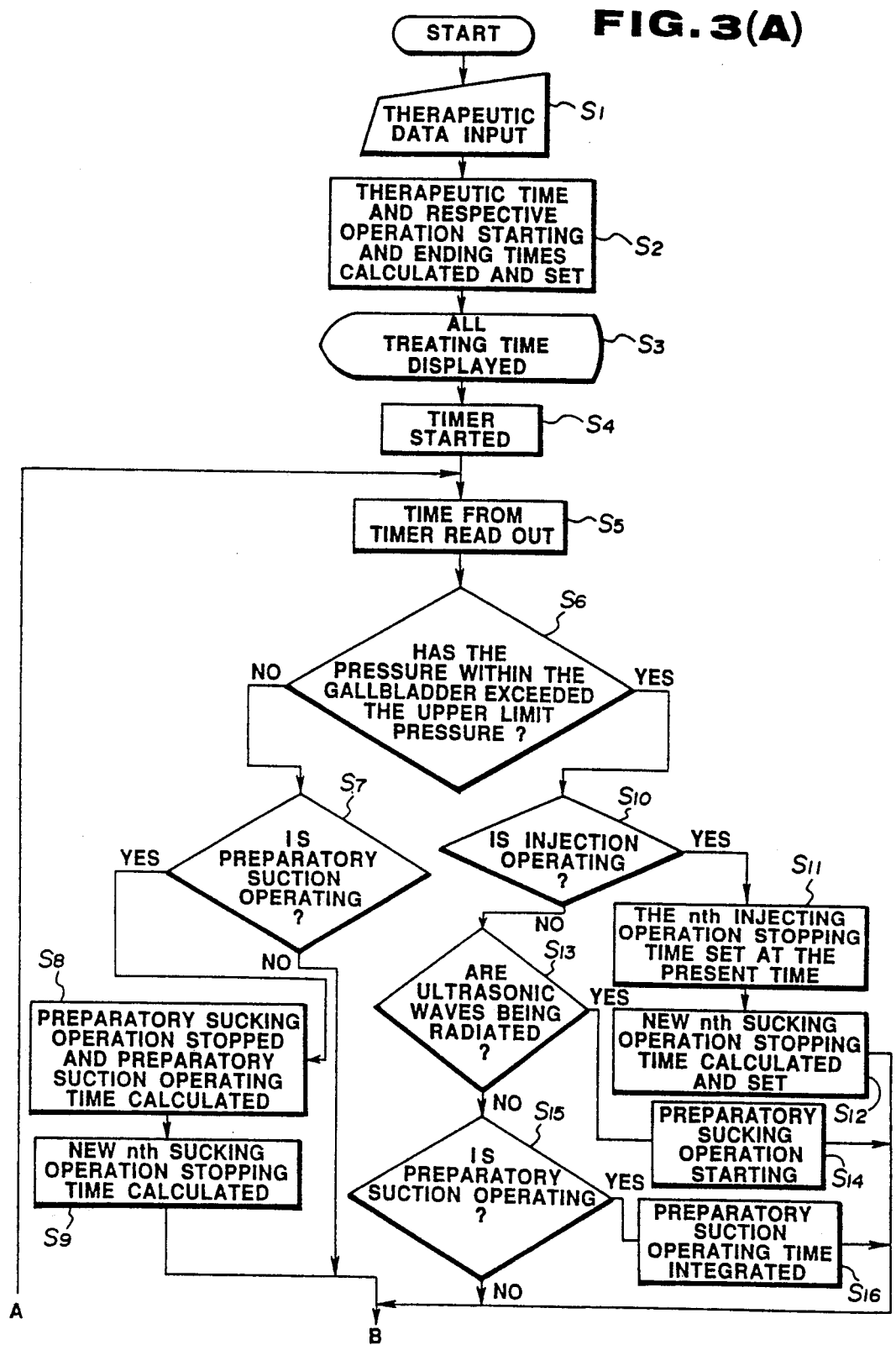
FIGS. 3(A) and (B) are flow charts showing the operation of the dissolving therapeutic apparatus.

Here, the detailed operation of the inputting and controlling apparatus 20 shall be explained with reference to FIGS. 3(A) and (B). By the way, FIGS. 3(A) and (B) are continued to each other at the reference symbols A and B.

When the operation of the dissolving therapeutic apparatus 1 starts, first, in the step S1 (mentioned merely as S1 by omitting the word "step" hereinafter), the operator inputs data required for the therapy. That is to say, the medicinal liquid injecting (sucking) time or injecting (sucking) amount, the ultrasonic wave radiating time or the leaving time, the pausing time as required and the number of repetitions of a series of injecting, leaving and sucking operations are input into the inputting and controlling apparatus 20 by the operator. Then, in S2, the treating time and respective operation starting and ending times are calculated and set. That is to say, the time required for the therapy (all treating time) is calculated on the basis of the data input in S1. Also, such operation starting and ending times of the respective operating means (for example, the injection pump 10, suction pump 11 and ultrasonic applicator 14) over all the therapy as the n th injection starting time, the injection ending and ultrasonic radiation (or leaving) starting times, the ultrasonic radiation (or leaving) ending and suction starting times, the suction ending and pause starting times and the pause ending, that is, the n+1 th injection starting time are calculated and are set and memorized in the inputting and controlling apparatus 20. The respective operations are switched on the basis of said times.

Then, in S3, the time (all treating time) required for the therapy and calculated in S2 is displayed in the displaying part 20a of the inputting and controlling apparatus 20.

Then, in S4, in order to control the treating time, the timer within the inputting and controlling apparatus 20 is started so that the time (the lapsing time after the start of the therapy) at any point may be known as required. In S5, the time is read out of the timer.

Then, in S6, it is judged whether the pressure within the gallbladder has exceeded the upper limit pressure or not. The pressure within the gallbladder is measured by the pressure sensor 9. The measured result is input into the comparing circuit 36 through the signal amplifier 30 and low-pass filter 32 within the controlling unit 19 and is compared with the reference voltage of the reference voltage source 35 corresponding to the upper limit pressure value in this comparing circuuit 36. By the output state, that is, "H" or "L" of this comparing circuit 36, it is judged whether the pressure within the gallbladder has exceeded the upper limit pressure or not.

In the case of NO in said S6, in S7, it is judged whether a preparatory suction is operating or not. The preparatory suction is to operate the suction pump 11 until the pressure within the gallbladder becomes below the set upper limit value to remove the excess pressure when the pressure within the gallbladder has exceeded the set upper limit pressure while the ultrasonic waves are being radiated or while the liquid is left. In the case of NO in this S7, the operation proceeds to S17. On the other hand, in the case of YES in S7, in S8, the Preparatory sucking operation is stopped and the preparatory sucking operation time is calculated. Concretely, the suction pump 11 is stopped and the time while the suction pump 11 has operated is determined. Then, in S9, the new n th sucking operation stopping time is calculated and the operation proceeds to the S17. In the S9, the suction pump stopping time in the sucking operation is determined so that:

[Injecting operation time (operating time of injection pump 10)] = [Preparatory sucking operation time] + [Sucking operation time].

In the case of YES in the S6, by the following S10, S13 and S15, the operating state at the time when the pressure within the gallbladder exceeds the upper limit pressure is judged. First, in S10, whether the injection is operating or not is judged. In the case of YES in this S10, in S11, the n th injecting injecting operation stopping time is set at the present time. When the injecting operation stopping time is thus set at the present time taken in in S5, though the injection pump 10 stopping time is inherently yet later, in the later described S21 and S22, the injecting operation will be stopped. Thus, when the pressure within the gallbladder has exceeded the upper limit pressure, if the injection is operating, the injecting operation will be stopped at once. Then, in S12, the new n th sucking operation stopping time is calculated and set and the operation proceeds to the S17. That is to say, on the basis of the actual injecting time until the injection is stopped by an abnormal pressure, the new n th suction stopping time is set so that

[Actual injecting time] = [Sucking time].

In the case of NO in the S10, in S13, it is judged whether the ultrasonic waves are being radiated (or the liquid is left) or not. The ultrasonic wave radiation means that ultrasonic waves are radiated into the body from the ultrasonic wave applicator 14. In the case of YES in this S13, in S14, the preparatory sucking operation is started and the operation proceeds to the S17. Concretely, the suction pump 11 is operated.

In the case of NO in said S13, in S15, it is judged whether the preparatory suction is operating or not. In the case of YES, in S16, the preparatory suction operating time is integrated and the operation proceeds to the S17. That is to say, the time when the suction pump 11 is operating for the preparatory suctiion is integrated at each reading out in S5. In the case of NO in the S15, the operation proceeds to S17.

In the S17, it is judged whether the n th injecting operation starting time or not. By the way, the injecting operation start means to start the operation of the injection pump 10. In the case of YES in the S17, in S18, it is judged whether the pressure within the gallbladder has exceeded the upper limit pressure or not. In the case of NO, in S19, the operation of the injection pump is started and the operation proceeds to S30. In the case of YES, in S20, the abnormal pressure is made known and the operation proceeds to S30. At the time of starting the injecting operation, if the pressure within the gallbladder has exceeded the upper limit pressure, by the processes of S18 and S20 and the processing speed, the injection pump 10 will not rotate and the abnormality will be made known.

In the case of NO in said S17, in S21, it is judged whether the n th injecting operation stopping time or not. In the case of YES, in S22, the injection pump 10 is stopped and the ultrasonic wave radiation or the leaving is started and the operation proceeds to the S30.

In the case of NO in said S21, in S23, it is judged whether the n th sucking operation starting time or not. In the case of YES, in S24, it is judged whether the preparatory sucking operation has ended or not. In the case of YES, the operation proceeds to S27. In the case of NO in this S24, in S25, the preparatory sucking operation is stopped and the preparatory sucking operation time is calculated. In S26, the new n th sucking operation stopping time is calculated and the operation proceeds to S27. Thus, in S24, S25 and S26, in case the sucking operation is entered while the preparatory sucking operation has not ended, the same as in S8 and S9, the suction pump 11 operating time until then is determined as the preparatory sucking time and the preparatory suction is stopped.

In the S27, the ultrasonic wave radiation or the leaving is stopped and the sucking operation is started. The operation proceeds to said S30. By the way, the sucking operation start is to start the operation of the suction pump 11.

In the case of NO in the S23, in S28, it is judged whether the n th sucking operation stopping time or not. In the case of NO, the operation proceeds to S30. In the case of YES, in S29, the operation of the suction pump 11 is stopped and the operation proceeds to said S30.

In said S30, it is judged whether the n th pausing operation ending time or not. That is to say, here it is judged whether the sequence of one unit has ended or not. In the case that no pausing time is provided, the sucking operation ending time and the pausing operation ending time coincide with each other. In the case of NO in S30, the operation returns to S5. In the case of YES, in S31, it is judged whether the set number of repetitions has ended or not. That is to say, here it is judged whether the number of the repeated sequences has reached the set number or not. In the case of NO in this S31, in S32, the number of repetitions of the therapy is counted up. That is to say, n=n+1 and the operation returns to S5. That is to say, in S32, one of the variables showing the numbers of repetitions of the sequence carried out to make the next sequence is counted up.

In the case of YES in the S31, in S33, the therapeutic data are preserved and the operation ends. That is to say, in S33, such therapeutic operation results as the actually injected time and amount or sucked time and amount, the left or ultrasonic wave radiated time and the number of actual repetitions in each sequence are preserved in the inputting and controlling apparatus 20.

Thus, in the dissolving therapeutic apparatus 1 of this embodiment, with the start of the operation, such therapeutic data as, for example, the injecting (sucking) time, ultrasonic wave radiating time, pausing time and number of repetitions are input by the operator into the inputting and controlling apparatus 20 which calculates, sets and records the operation starting and ending time of the respective operating means through a series of repeated operations from the start to the end of the therapy on the basis of the input data, that is, the operating times of the respective operating means (such as the injection pump 10 and suction pump 11). Then, the inputting and controlling apparatus 20 starts a timer for reading out time and starts the operation of a therapeutic loop by which first the time is read out, it is judged whether the pressure within the gallbladder has exceeded the upper limit pressure value set by the controlling unit 19 or not and, in case it has exceeded the upper limit pressure value, a treatment will be made in response to the operating condition then. Then, by the treatment by judging the coincidence of the read time and the respective operation switching time with each other, the respective operations of the injection, ultrasonic wave radiation (leaving), suction and pause are switched and this loop is repeated until the pausing time ends. When one sequence formed of a series of operations of the suction, ultrasonic wave radiation (leaving), suction and pause ends, the parameters (variables) used in one operation are initialized and are operated to again enter the therapeutic loop until the set number of repetitions ends.

Therefore, in the dissolving therapeutic apparatus 1 of this embodiment, the respective operations are started and ended by the time control based on the switching time. When the pressure within the gallbladder exceeds the set upper limit value, said switching time is varied and the operation is switched by pressure by utilizing the operation flow of the time control. That is to say, such time control as makes higher the control by the pressure within the gallbladder is made.

Thus, in the dissolving therapeutic apparatus 1 of this embodiment, basically the time operation is controlled and further the operation by the pressure within the gallbladder is controlled prior to it. Therefore, the control mode will change in the operation of one cycle of the injection, ultrasonic wave radiation (leaving), suction and pause. That is to say, when the pressure value becomes abnormal, the control parameter of the time control will be changed and the operation will be switched by utilizing the operation algorithm of the time control.

Therefore, in this embodiment, in order to switch the respective operations by the start and end in the set time and to change this set time by the prior control by the pressure, a therapeutic time axis is provided so that the times of switching the respective operations may be all allotted on said therapeutic time axis.

The reason therefor is because, as the operation starting and ending times will be made to fall forward by the pressure control, unless an absolute time axis is provided, the time control will become indefinite. Also, such so-called "falling domino system" control as "after some operation is made for some seconds, the next operation is made for some seconds" is a method so likely to mis-operate as to be very dangerous and to be absolutely avoided.

The method of the time control adopted in this embodiment and making the control by the pressure above can be summarized to the following two points that the respective operations are started and ended according to the switching time allotted to the therapeutic time axis and that, when the pressure value becomes abnormal, the allotted time will be changed and the operation will be switched by utilizing the algorithm of the time control.

Figure 4:
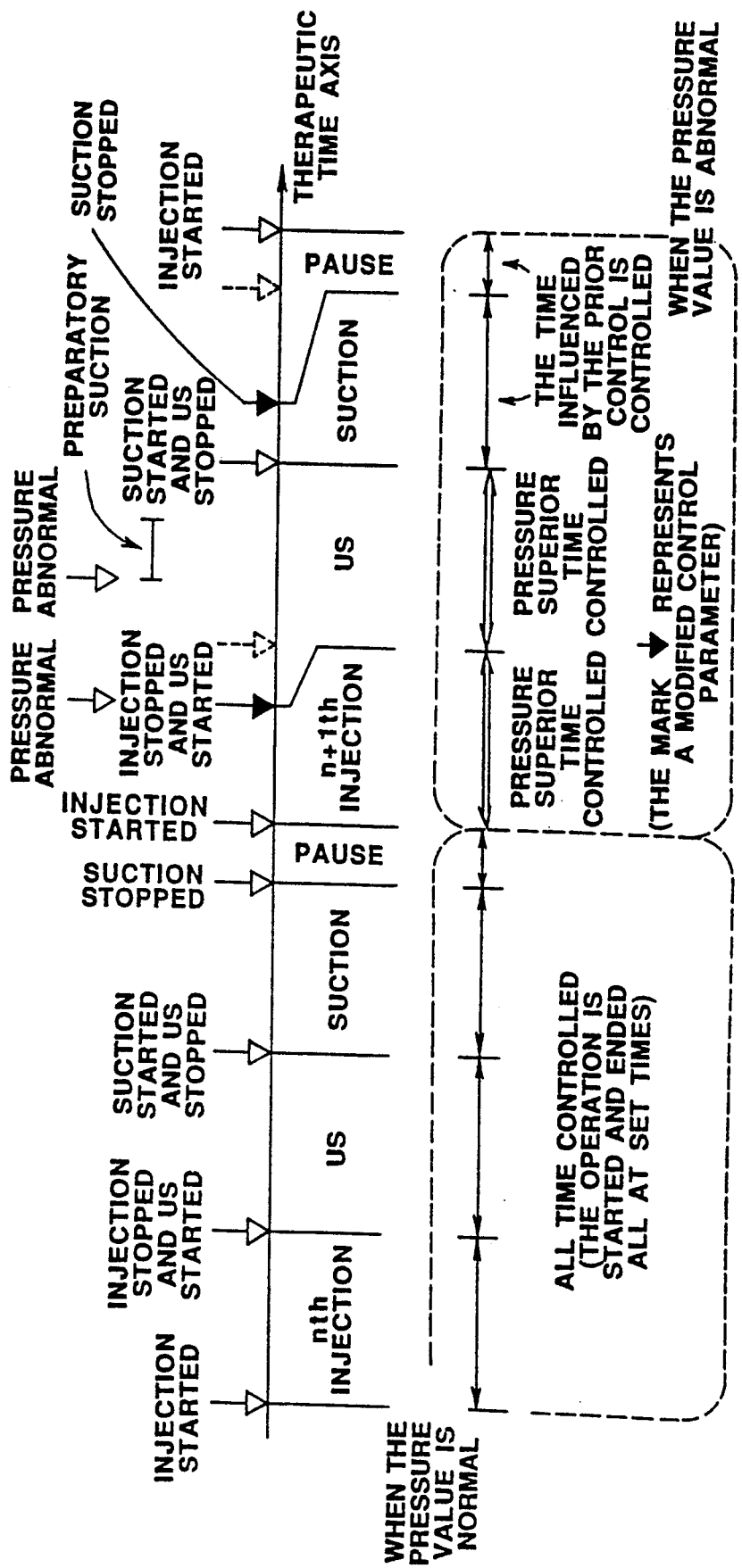

Here, the sequence of the dissolving therapeutic apparatus and an example of the change of the parameter when the pressure value is abnormal shall be explained in FIG. 4.

On the left side of FIG. 4 is shown one sequence in the case that the pressure value is normal and on the right side is shown the case that the pressure value is abnormal. One sequence is formed of four operations of the injection, ultrasonic wave radiation (mentioned as US in FIG. 4), suction and pause. In case the pressure value is normal, all the operations are made by the time control and the respective operations are all switched to the set times in starting and ending. On the other hand, In case the pressure value is abnormal, a partly pressure superior time control is made. In the example in FIG. 4, as the pressure becomes abnormal at the time of the n+1 th injecting operation, the injection stopping and ultrasonic wave radiation starting times (control parameters) are changed and the injecting and ultrasonic wave radiating operations are pressure superior time-controlled. Further, the pressure becomes abnormal at the time of the ultrasonic wave radiation, a preparatory sucking operation is made, therefore the suction stopping time is changed and the sucking and pausing operations are time-controlled under the influence of the prior control.

Figure 5:
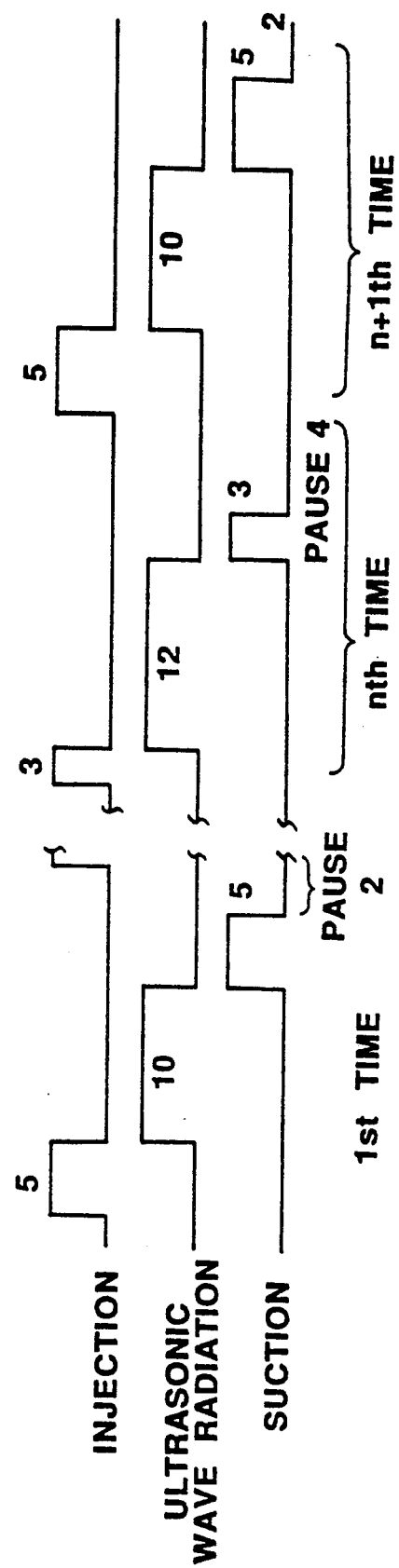

Also, in this embodiment, the parameter change by the pressure control in any sequence will not influence the next sequence. This shall be explained with reference to FIG. 5.

In the dissolving therapeutic apparatus 1 of this embodiment, in case the pressure within the gallbladder does not exceed the set upper limit value, on the basis of the respective operating times of the injection, ultrasonic wave radiation and suction input and set with the operation start of the apparatus, the therapeutic operation is controlled in the time. In the example in FIG. 5, the times of the respective operations are represented by 5 for the injection, 10 for the ultrasonic wave radiation, 5 for the suction and 2 for the pause. In the n th sequence, during the injection or the ultrasonic wave radiation, even if the pressure within the gallbladder exceeds said set upper limit value and the above described operating time is changed to prefer the pressure, one sequence making time will not change. In the example in FIG. 5, the time is changed to 3 for the injection, therefore, to 12 for the ultrasonic wave injection, 3 for the suction and 4 for the pause. One sequence making time does not change. In the next n+1 th sequence, in case the operating time does not change with the preference of the pressure within the gallbladder, the respective operating time will follow the operation starting and ending times by the operating times input and set with the operation start of the dissolving therapeutic apparatus 1.

Thus, in the dissolving therapeutic apparatus 1 of this embodiment, even if the operating times are changed with the preference of the pressure within the gallbladder, the sequence making time will not change and will not influence the respective operating times and the respective operation starting and ending times. Therefore, the therapy can be stably made for a predetermined time without being influenced by the condition of the treated part.

Figure 6:
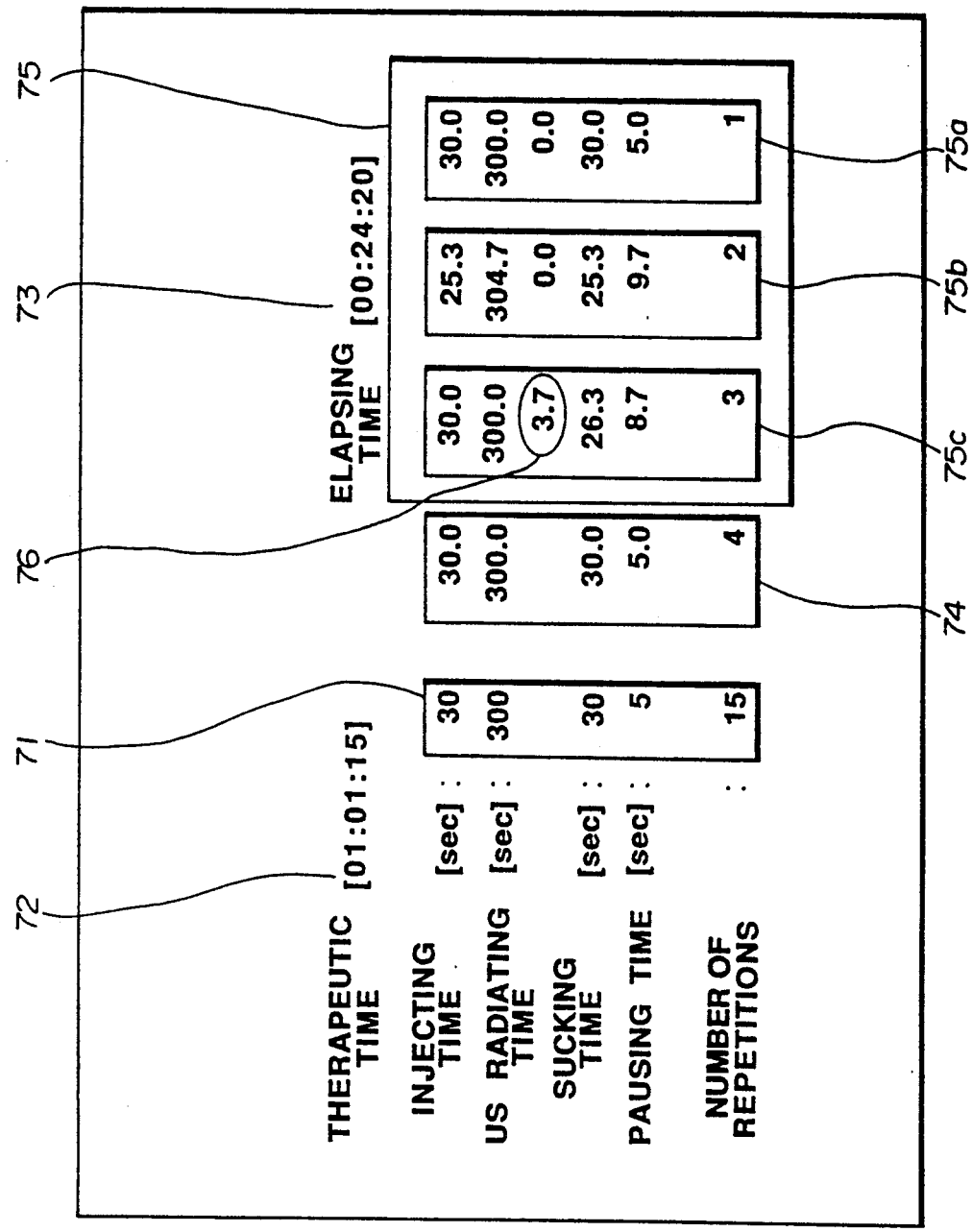

The setting of the respective operating times and the display of the therapeutic contents at the time of the therapeutic operation shall be explained in the following with reference to FIG. 6 showing a displaying part 20a of the inputting and controlling apparatus 20. By the way, in FIG. 6, the ultrasonic wave radiating time is mentioned as a US radiating time.

In this embodiment, at the time of starting the operation of the dissolving therapeutic apparatus 1, the operator inputs and sets the injecting time, ultrasonic wave radiating time, pausing time and number of repetitions. The ultrasonic wave radiating time, that is, the medicinal liquid leaving time is set on the basis of such dissolving conditions as the size of the coagulation and the kind of the medicinal liquid. By the way, the sucking time is automatically set so as to be equal to the injecting time. The times for setting these respective operations are displayed in the displaying part 20a of the inputting and controlling apparatus 20. On the basis of the thus set values, the starting times, ending times and all treating times of the respective operations are calculated.

During the therapy, the set times for the respective operations are displayed in the region shown by the reference numeral 71 in FIG. 6 and all the treating time is displayed in the region shown by the reference numeral 72. Also, in response to the operation, the therapeutic elapsing time is displayed in the region shown by the reference numeral 73. The elapsing times of the respective operations are displayed in the region shown by the reference numeral 74.

Further, the operating time data of the past three therapeutic cycles are scroll-displayed in the region shown by the reference numeral 75. By the way, in FIG. 6, in case the fourth cycle is now operating, the respective operating time data of the first, second and third cycles will be displayed respectively in the regions shown by the reference numerals 75a, 75b and 75c.

For example, as in said third cycle, in case the preparatory suction operates during the ultrasonic wave radiation, the preparatory suction time will be displayed in the region shown by the reference numeral 76 between the ultrasonic wave radiating time displaying region and the sucking time displaying region.

Figure 3B:
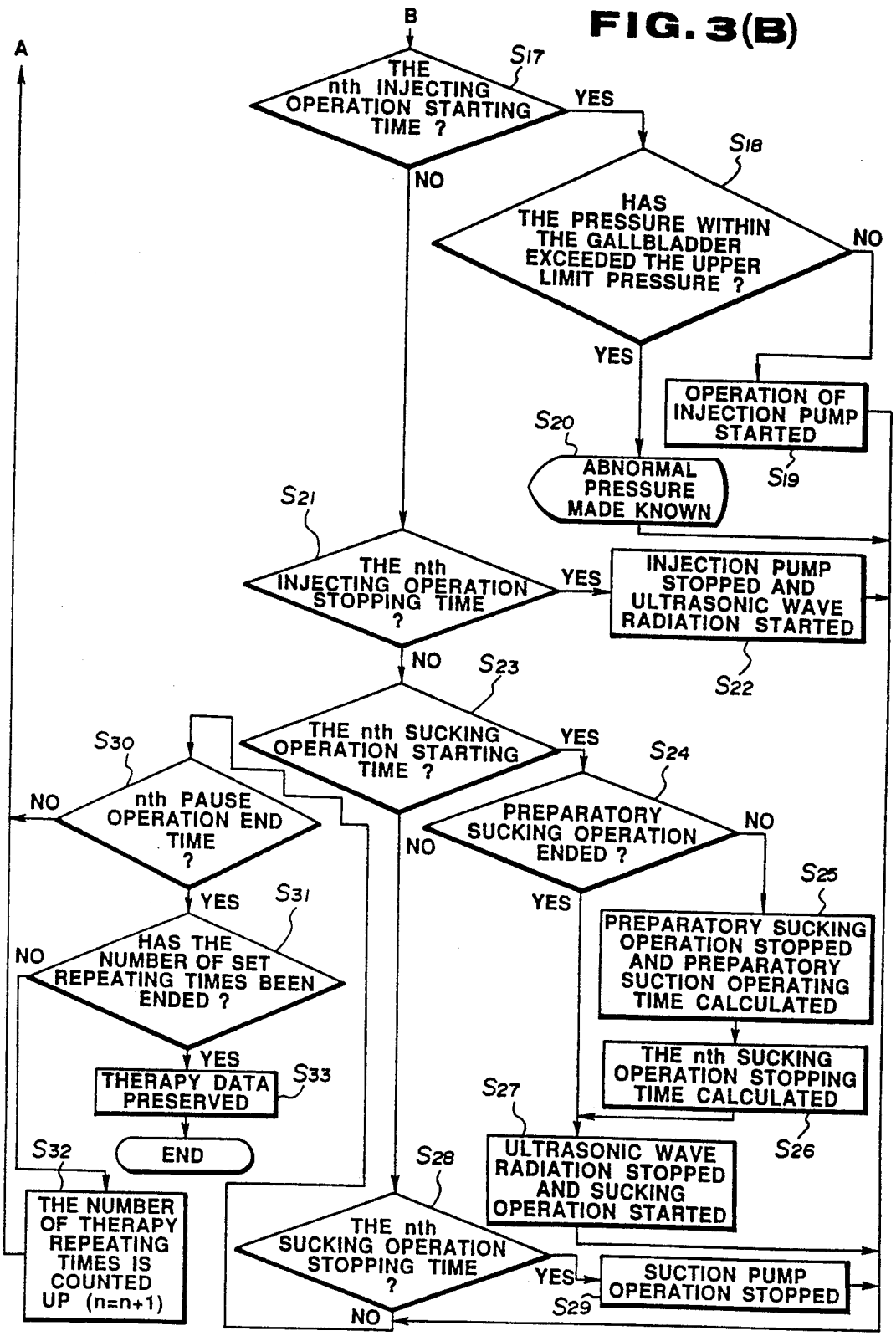

Also, the notification of the abnormal pressure in S20 in FIG. 3(B) is displayed in said displaying part 20a. By the way, together with the abnormal pressure notification display, a warning sound may be issued.

In a conventional dissolving therapeutic apparatus, a predetermined therapy is only made and all the therapeutic time can be set at most but the respective operating times can not be set and the operator can not catch the therapeutic contents in detail and can not concretely operate the therapeutic contents. Therefore, it has been impossible to make a therapy adapted to each patient.

On the other hand, according to this embodiment, the details of the therapy can be set and the therapeutic pattern most adapted to each patient can be set. The entire manner of the therapy and the detailed manners of the respective operations of the detailed parts can be caught.

By the way, the parameters of the injecting operation and sucking operation may be made by the injected amount (in cc.) and sucked amount (in cc.) instead of the time and the injected amount and sucked amount may be displayed in the displaying part 20a.

The numbers of rotations of the injection pump 10 and suction pump 11 may be predetermined, may be input or may be automatically detected. In the inputting and controlling apparatus 20, even in case the parameters of the input or displayed injection and suction are made the amounts, the actually controlling parameters will be the times. That is to say, the inputting and controlling apparatus 20 calculates the injection time and suction time from the number of rotations of the pump and the set injected amounte and sucked amount. Therefore, in the dissolving therapeutic apparatus 1 of this embodiment, even in case the parameters of setting the injecting and sucking operations are made the amounts, the same treatment as in the setting by the time will be able to be made. Thus, in this embodiment, whatever the parameters of the input and display may be, the operation controlling parameter is made by the time. Therefore, the setting by the input amount and sucked amount can be said to be the setting of the injecting time and sucking time. On the contrary, the setting by the injecting time and sucking time can be also said to be the setting of the injected amount and sucked amount.

The sequence of the time set by the inputting and controlling apparatus 20 and formed of the above described medicinal liquid injecting time, the therapeutic ultrasonic wave radiating time, the time of sucking the fluid sucked from the gallbladder 4 and the pausing time set as required and three operation examples shall be explained in the following by using FIGS. 7 to 9.

FIG. 7 shows the first example.

In FIG. 7, (A) shows the variation of the pressure of the gallbladder 4 by the medicinal liquid or the like injected into the gallbladder 4, (B) shows the operation and stop of the injection pump 10, (C) shows the operation and stop of the ultrasonic wave radiation by the ultrasonic wave applicator 14 and (D) shows the operation and stop of the suction pump 11 respectively on the same time axis. By the way, in FIGS. 7 (A) to (D), the two-point chain line shows a set sequence and the solid line shows an actual operation. In this example, no pausing time is provided.

On the basis of the time set in the inputting and controlling apparatus 20, a driving signal is input into the operation adjusting circuit 39 within the controlling unit 19, the injection pump 10 rotates at the number of rotations set in the controlling unit 19 and the medicinal liquid is injected into said gallbladder 4.

After the injection of the above described medicinal liquid ends, the medicinal liquid is left within the gallbladder 4 and, on the basis of the intensity and time set in the controlling unit 19 and inputting and controlling apparatus 20, the therapeutic ultrasonic waves are radiated into said gallbladder 4.

After the above described therapeutic ultrasonic wave radiation ends, the suction pump 11 is driven at the number of rotations and time set in the controlling unit 19 and inputting and controlling apparatus 20 and a fluid containing the used medicinal liquid is discharged out of the body.

The above described medicinal liquid is injected and sucked by the reference voltage sources 35 and 37 within the controlling unit 19 in the range not exceeding the preset upper limit pressure by the medicinal liquid or the like within the gallbladder 4 and the lower limit pressure by the suction.

For example, during the therapy, in case the state of the gallbladder 4 varies and the allowable capacity of the gallbladder 4 becomes small, before the prescribed injecting time ends, as shown by the reference symbol a in FIG. 7(A), the pressure by the medicinal liquid or the like of the gallbladder 4 will exceed the set upper limit. At this time, a signal showing such state will be output to the inputting and controlling apparatus 20 from the comparing circuit 36 within the controlling unit 19. As shown by the reference symbol b in FIGS. 7(B) and (C), the inputting and controlling apparatus 20 respectively controls the operation adjusting circuit 39 and output adjusting circuit 43 to stop the operation of the injection pump 10 and to start the operation of radiating therapeutic ultrasonic waves to said gallbladder 4 from the ultrasonic wave applicator 14.

The time for sucking the fluid containing the medicinal liquid becomes the time equal to the actual injection operating time. By the way, also at the sucking time, in case the pressure within said gallbladder 4 has exceeded the lower limit as shown by the reference symbol c in FIG. 7(A), a signal showing such state will be output to the controlling apparatus 20 from the comparing circuit 38 within the controlling unit 19 and the following control may be made. That is to say, as shown by the reference symbol d in FIG. 7(D), the controlling apparatus 20 controls the operation adjusting circuit 41 to stop the suction pump 11. Then, until the time when the next sequence (injection of the medicinal liquid) is started, the dissolving therapeutic apparatus 1 is let to stand by.

FIG. 8 shows the second example. FIG. 9 shows the third example.

In FIGS. 8 and 9, (A) shows the variation of the pressure of the gallbladder 4 by the medicinal liquid or the like injected into the gallbladder 4, (B) shows the operation and stop of the injection pump 10,(C) shows the operation and stop of the ultrasonic wave radiation by the ultrasonic wave applicator 14 and (D) shows the operation and stop of the injection pump 10 respectively on the same time axis.

The same as in the above described first example, when the injection of the medicinal liquid ends and the therapeutic ultrasonic waves are being radiated, as shown by the reference symbol e in FIG. 8(A), in case the pressure by the medicinal liquid or the like of the gallbladder 4 has exceeded the set upper limit, a signal showing such state will be output to the inputting and controlling apparatus 20 from the comparing circuit 36 within the controlling unit 19. As shown by the reference symbol f in FIG. 8(D), the inputting and controlling apparatus 2 controls the operation adjusting circuit 41 to drive the suction pump 11 to suck the fluid from the gallbladder 4 until the pressure by the medicinal liquid and the like of the gallbladder 4 becomes below the upper limit pressure. That is to say, the preparatory suction is made. By the way, at this time, the ultrasonic wave radiation by the ultrasonic wave applicator 14 will be simultaneously made.

Then, in the case of sucking the fluid containing the medicinal liquid within the gallbladder 4 by an ordinary sequence, so that the sum of the sucking time and the prior preparatory sucking time may coincide with the injecting time in the sequence, in the inputting and controlling apparatus 20, as shown by the reference symbol g in FIG. 8(D), a new sucking operation time is determined and the operation adjusting circuit 41 is controlled to drive said suction pump 11.

Also, when the injection of the medicinal liquid has ended and the therapeutic ultrasonic waves are being radiated as described above, as shown by the reference symbols $e_1$ and $e_2$ in FIG. 9(A), even when a plurality of cases that the pressure by the medicinal liquid and the like of the gallbladder 4 has exceeded the set upper limit occur, the same as in the operation explained by using FIG. 8, as shown by the reference symbols $f_1$ and $f_2$ in FIG. 9(D), the suction pump 11 will be driven and the preparatory suction will be made until the pressure by the medicinal liquid and the like of the gallbladder 4 becomes below the upper limit pressure.

Then, the same as in the operation explained by using FIG. 8, in the case of sucking the fluid containing the medicinal liquid within the gallbladder 4 by an ordinary sequence, so that the sum of the sucking time and the prior preparatory sucking time may coincide with the injecting time in the sequence, as shown by the reference symbol g' in FIG. 9(D), a new sucking operation time will be determined and the suction pump 11 will be operated.

That is to say, in the dissolving therapeutic apparatus of this example, even in case the therapeutic ultrasonic waves are being radiated to the gallbladder 4, when the pressure by the medicinal liquid and the like of the gallbladder 4 rises due to such external turbulances as the motion and breath of the human body 2, the preparatory suction will be made so that the pressure by the medicinal liquid and the like of the gallbladder may not exceed the upper limit. Thus, there are effects that a safe therapy can be continued and that, in each sequence, the fluid containing the injected medicinal liquid injected into the gallbladder 4 can be positively sucked.

Also, according to this embodiment, as at least the three steps of the injection, leaving and suction are repeated, the contact of a new dissolving agent with the coagulation will be accelerated and the dissolving efficiency will be high. Further, in consideration of the time when the medicinal liquid dissolves the coagulation, the leaving step is provided, therefore the injecting and sucking operations by the pump can be reduced without reducing the dissolving effect and the medicinal liquid can be prevented from flowing out of the treated part.

As the fluid sucked from the treated part is not again injected into the treated part but a new medicinal liquid is injected, the dissolving efficiency is always high.

According to this embodiment, further, lest the medicinal liquid should leak out of the treated part, the pressure by the medicinal liquid and the like within the gallbladder 4 is detected so that, in case this pressure becomes abnormal, the protocol of the above described sequence may be controlled to be automatically changed and the amount of the fluid within the treated part may be adjusted. Therefore, there is an effect that a safe therapy can be made.

Also, in the leaving step, when the ultrasonic waves are radiated toward the coagulation, even in the leaving state, the dissolution will be able to be accelerated and the dissolving efficiency will improve. As the dissolution is accelerated by the ultrasonic wave radiation, the leaving time can be made long without reducing the dissolving efficiency.

According to this embodiment, the delicate pressure value which can not be adjusted even by moving the pressure sensor 9 in the vertical direction on the rail 27 can be electrically adjusted by the offset adjusting means 31 and, by the offset pressure displaying circuit 34, a delicate offset adjustment can be made while recognizing a positive offset value. Thus there is an effect that a safer therapy can be made.

FIG. 10 shows the second embodiment of the present invention. By the way, the formation of the dissolving therapeutic apparatus is the same as in the above described first embodiment and only the sequence shall be explained by using the same reference numerals. In FIG. 10, (A) represents the variation of the pressure of the gallbladder 4 by the medicinal liquid and the like injected into the gallbladder 4, (B) represents the operation and stop of the injection pump 10, (C) represents the operation and stop of the ultrasonic wave radiation by the ultrasonic wave applicator 14 and (D) represents the operation and stop of the suction pump 11 respectively on the same time axis.

For example, there is a case that the living body 2 moves, the volume of the gallbladder 4 varies and the pressure by the medicinal liquid and the like of the gallbladder 4 reduces as shown by the reference symbol $e_3$ in FIG. 10(A).

In this embodiment, the sequence is such that, in case the pressure by the medicinal liquid and the like of the gallbladder 4 reduces as described above, the inputting and controlling apparatus 20 will detect the state by said pressure sensor 9, will drive said injection pump 10 as shown by the reference symbol $f_3$ in FIG. 10(B) and will further inject the medicinal liquid. This injection shall be called a preparatory injection hereinafter. By the way, the sudden reduction of the pressure within the gallbladder can be detected from the variation rate of the monitored output from the pressure detecting means.

Then, the same as in the above described first embodiment, by an ordinary sequence, in the case of sucking the fluid containing the medicinal liquid within the gallbladder 4, so that the sum of the suction time and the prior preparatory suction time may coincide with the sum of the injection time and the preparatory injection time in the sequence, as shown by the reference symbol g" in FIG. 10(D), a new sucking operation time will be determined and the suction pump 11 will operate.

That is to say, in the dissolving therapeutic apparatus of this embodiment, even in case therapeutic ultrasonic waves by such external turbulences as the action and breath of the human body 2 are being radiated to the gallbladder 4, when the pressure by the medicinal liquid and the like of the gallbladder 4 reduces, a preparatory injection will be made so that the pressure by the medicinal liquid and the like of said gallbladder may be of a predetermined value. Thus there are effects that the dissolution of the coagulation can be accelerated and the fluid containing the medicinal liquid injected into the gallbladder 4 in each sequence can be positively sucked.

The other formations, operations and effects are the same as in the first embodiment.

FIGS. 11 and 12 show the third embodiment of the present invention. By the way, the formation of the dissolving therapeutic apparatus is the same as in the above described embodiment and only the sequence shall be explained by using the same reference symbols.

In FIGS. 11 and 12, (A) represents the variation of the pressure of the gallbladder 4 by the medicinal liquid and the like injected into the gallbladder 4, (B) represents the operation and stop of the injection pump 10, (C) represents the operation and stop of the ultrasonic wave radiation by the ultrasonic wave applicator 14 and (D) represents the operation and stop of the suction pump 11 respectively on the same time axis.

Even during the above described therapeutic treatment, the body liquid will flow into the treated part in most cases. For example, the gall will flow into the gallbladder 4.

Such gall is larger in the specific gravity than the medicinal liquid. Therefore, within the gallbladder 4, the above described medicinal liquid will separate upward and the gall will separate downward. Therefore, the gallstone 5 will become so small in the area contacting the medicinal liquid that the efficiency of the dissolving therapy will reduce.

The amount of the medicinal liquid that can be injected will be an amount after the amount of the gall which has flowed to be accumulated in the gallbladder 4 is subtracted, that is to say, the amount of said medicinal liquid will become small and thereby the efficiency of the dissolving therapy will be reduced.

Therefore, the reduction of the efficiency of the dissolving therapy by this gall can not be neglected.

Therefore, in the dissolving therapeutic apparatus of this embodiment, as shown in FIG. 11, a pausing period is provided between the sucking period and injecting period in the sequence.

In the above described pausing period, as shown by the reference symbol h in FIG. 11(A), after the suction in the ordinary sucking period, the pressure by the medicinal liquid and the like within the gallbladder 4 is detected. Such pressure shall be called a residual pressure hereinafter.

As shown by the reference symbol j in FIG. 11(D), the inputting and controlling apparatus 20 controls the operation adjusting circuit 41 so that the residual pressure present in the gallbladder 4 may be zero. Thereby, the suction pump 11 will be driven by the operation adjusting circuit 41. In such case, the pressure of the gallbladder 4 is monitored by the controlling apparatus 20 so as not to be of the lower limit value set in advance.

FIG. 12(A) shows an example of the case that the pressure has risen by the inflow of the body liquid. In case such inflow amount of the body liquid can be predicted in advance, as shown by the reference symbol k in FIG. 12(D), the time of sucking the body liquid may be made a sequence provided in the pausing period. Even in this case, the pressure of the gallbladder 4 will be monitored by the controlling apparatus 20 so as not to be of the lower limit value set in advance.

That is to say, in the dissolving therapeutic apparatus of this embodiment, the fluid sucked from the gallbladder 4 and including not only the amount of the injected medicinal liquid but also the amount of the gallbladder having flowed to be accumulated within the gallbaldder 4 can be sucked and removed and there is an effect that the efficiency of the dissolving therapy can be elevated.

By the way, the pausing period may be provided once in several repetitions of the injection, ultrasonic wave radiation and suction. In this case, the pausing time at the time of providing the pausing period may be set at a predetermined value not zero and the pausing time at the time of providing no pausing period may be set at zero.

The other formations, operations and effects are the same as in the first embodiment.

FIG. 13 shows the fourth embodiment of the present invention. By the way, the same components as in the above described embodiment shall bear the same reference numerals and shall not explained here.

In the dissolving therapeutic apparatus of this embodiment, from the dissolving therapeutic apparatus of the above described embodiment, a catheter 96 is provided instead of the catheter 6, a connector 97 is provided instead of the connectors 7a and 7b, a pump tube 98 is provided instead of the injection pump tube 8a and suction pump tube 8b, a pump 46 and electromagnetic valve 50 are provided instead of the injection pump 10 and suction pump 11, an operation adjusting circuit 48 is provided instead of the operation adjusting circuits 39 and 41 and a rotation number and direction displaying circuit 49 is provided instead of the rotation number displaying circuits 40 and 42.

The catheter 96 having two lumina of an injecting and sucking pipeline 96a and pressure pipeline 96c is used.

Tubes 98a and 98b are connected respectively at one end to the electromagnetic valve 50 and are connected at the other ends respectively to a liquid tank 12 and discharged liquid tank 13.

The injecting and sucking pipeline 96a injects the medicinal liquid and sucks the fluid through the same pipeline.

The injecting and sucking pipeline 96a is connected to the pump tube 98 at one end through the connector 97.

The pump tube 98 has the pump 46 interposed in the intermediate part and is connected at the other end to the electromagnetic valve 50.

The pressure pipeline 96c is connected to the pressure sensor g.

The pump 46 and electromagnetic valve 50 are connected to the operation adjusting circuit 48.

The rotation number and direction displaying circuit 49 is further connected to the operation adjusting circuit 48.

The operation adjusting circuit 48 controls the rotating direction (injecting and sucking operation state) of the pump 46 and rotates and drives the pump 46. The direction and rotation number are displayed by the rotation number and direction displaying circuit 49.

Further, the operation adjusting circuit 48 drives said electromagnetic valve 50 to connect said tube 98 to the tube 98a or 98b.

The operation adjusting circuit 48 is controlled by the inputting and controlling apparatus 20 through the I/O interface 44 and bus line 45 explained in the above described embodiment.

An automatic-manual switching means 62 through a signal line 61 shown by a two-point chain line and an adjusting means 64 through a signal line 63 shown by a two-point chain line can be connected to the I/O interface 44.

By the automatic-manual switching means 62, the above described respective sequences are not automatically set but can be set by the adjusting means 64.

Thereby, there are effects that said medicinal liquid can be injected and the fluid containing the medicinal liquid can be sucked with one pump, the number of pumps can be saved, the sequence can be manually set and therefore the thickened mass dissolving therapy corresponding to the living body which is the patient can be made.

The other formations, operations and effects are the same as in the first embodiment.

By the way, in the above respective embodiments, the ultrasonic wave applicator and the means relating to driving the ultrasonic wave applicator are provided to elevate the efficiency of the dissolving therapy and the efficiency of the dissolving therapy may be elevated by using any other means.

Figure 15:
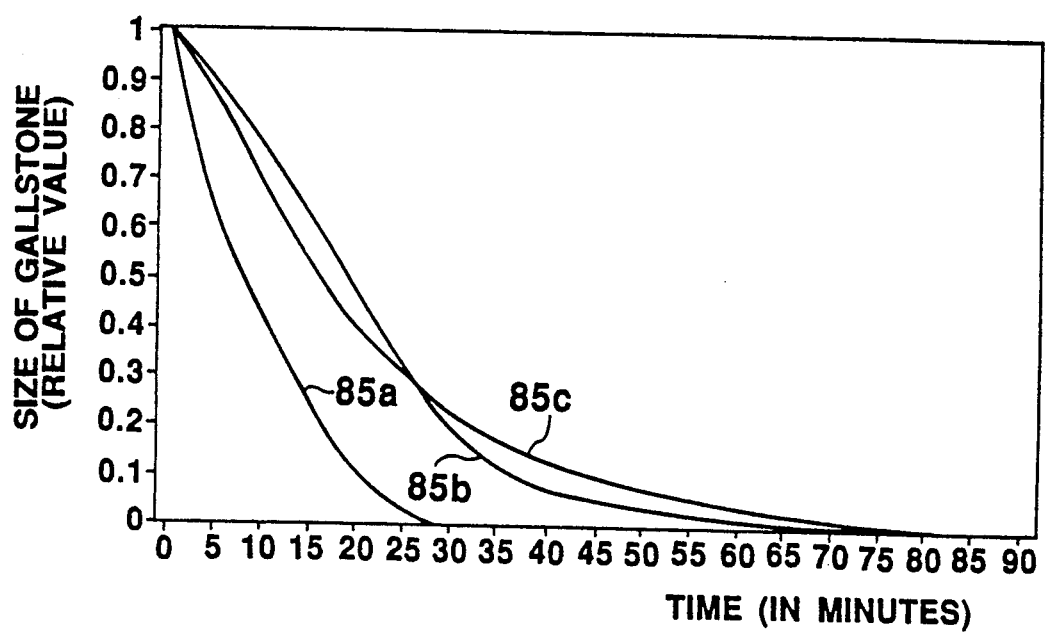

FIGS. 14 and 15 show the fifth embodiment of the present invention.

The summary of the dissolving therapeutic apparatus of this embodiment is the same as of the first embodiment.

In this embodiment, as shown in FIG. 14, the ultrasonic wave applicator 14 has three ultrasonic vibrators 14a, 14b and 14c. The output ends of a power amplifier 17 are connected to the ultrasonic vibrators 14a, 14b and 14c respectively through switches 86a, 86b and 86c of a switching means 86. The ultrasonic vibrators 14a, 14b and 14c are different from one another in the resonant frequency, for example, the resonant frequency of the ultrasonic vibrator 14a is 28 KH$_z$, the resonant frequency of the ultrasonic vibrator 14b is 40 KH$_z$ and the resonant frequency of the ultrasonic vibratorr 14c is 100 KH KH$_z$.

The later described output signal of an oscillator 18 is input into the power amplifier 17.

A signal adjusted and set on the frequency, amplitude, pulse number, pulse interval and driving time of the output signal is input into the oscillator 18 from a controlling unit 19. The output signal of this oscillator 18 is amplified by the power amplifier 17 and this amplified signal is applied to one of the ultrasonic vibrators 14a, 14b and 14c within the ultrasonic wave applicator 14 through one of the switches 86a, 86b and 86c of the switching means 86 controlled by said controlling unit 19.

Ultrasonic waves excited by one of the ultrasonic vibrators 14a, 14b and 14c are radiated to the vicinity including the stone 5 present within the gallbladder 4 of the human body 2.

Also, as shown in FIG. 13, by the control signal of the inputting and controlling apparatus 20 through the I/O interface 44 and bus line 45, for example, the frequency of the output signal of the oscillator 18 is controlled and this output signal is input into the output adjusting circuit 43, is adjusted, for example, in the amplitude, pulse number, pulse interval and driving time by the control signal of the inputting and controlling apparatus 20 through the I/O interface 44 and said bus line 45 in the output adjusting circuit 43, is then amplified by the power amplifier 17 and drives the ultrasonic vibrators 14a, 14b and 14c within the ultrasonic wave applicator 14 through the switching means 86 as described above.

By the signal input through the I/O interface 44 and the bus line 45, said inputting and controlling apparatus 20 operates the varying point of the ultrasonic image, for example, the signal level to detect the size of the stone 5 produced within the gallbladder 4 and controls the oscillator 18 and switching means 86 in response, for example, to the size of the stone or notifies the operator, for example, of the size of the stone 5 so that the operator may input by an input part not illustrated of the controlling unit 19 an instruction to control the oscillator 18 and switching means 86 in response to the size of the stone 5.

Here, the gallstone 5 dissolving time shall be explained by using FIG. 15 which shows an example of an experiment result showing the time (in minutes) on the abscissa and the rate of the size of the gallstone in the course of the therapy to the size of the gallstone before the therapy (in the relative value) on the ordinate.

First of all, FIG. 15 shall be explained. The reference numeral 85a represents the case that the medicinal liquid is injected into the ballbladder 4 and is left for a predetermined time and ultrasonic waves are radiated to the gallbladder 4 during the leaving time. The reference numeral 85b represents the case that the above described leaving time is not provided, the medicinal liquid is continuously injected into the gallbladder 4 and the fluid is discharged out of the gallbladder. The reference numeral 85c represents the case that the medicinal liquid is injected into the gallbladder 4 and is left for a predetermined time.

As understood even from the results of this experiment, in the reference numerals 85b and 85c, about 75 minutes are required until the dissolution is completed but, in the reference numeral 85, about 30 minutes are enough until the dissolution is completed.

Therefore, when a vibrating wave radiating step that the medicinal liquid is injected into the gallbladder 4 and is left for a predetermined time and ultrasonic waves are radiated to the gallbladder 4 during this leaving time is provided in the sequence of the inputting and controlling apparatus 20, the gallstone 5 dissolving time will be able to be reduced.

By the way, the ultrasonic wave applicator 14 may be internally provided with a single ultrasonic vibrator so that a plurality of the ultrasonic vibrators different in the resonant frequency may be replaced and used.

Thus, according to this embodiment, there are effects that, by the above described vibrating wave radiating step, the gallstone 5 dissolving time can be reduced and the therapeutic time can be reduced.

The other formations, operations and effects are the same as in the first embodiment.

Figure 16:
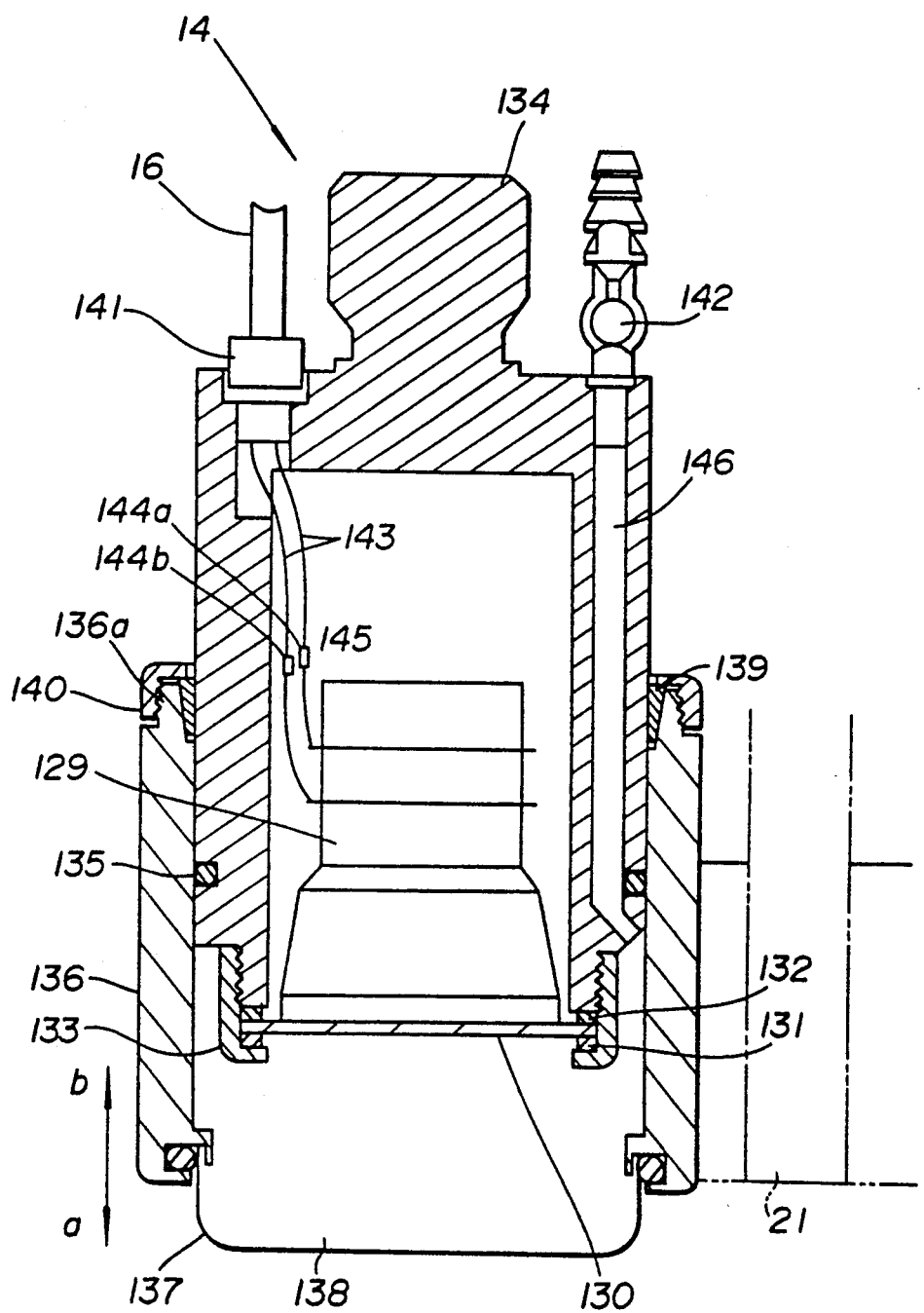
FIGS. 16 and 17 relate to the sixth embodiment of the present invention.
Figure 17:
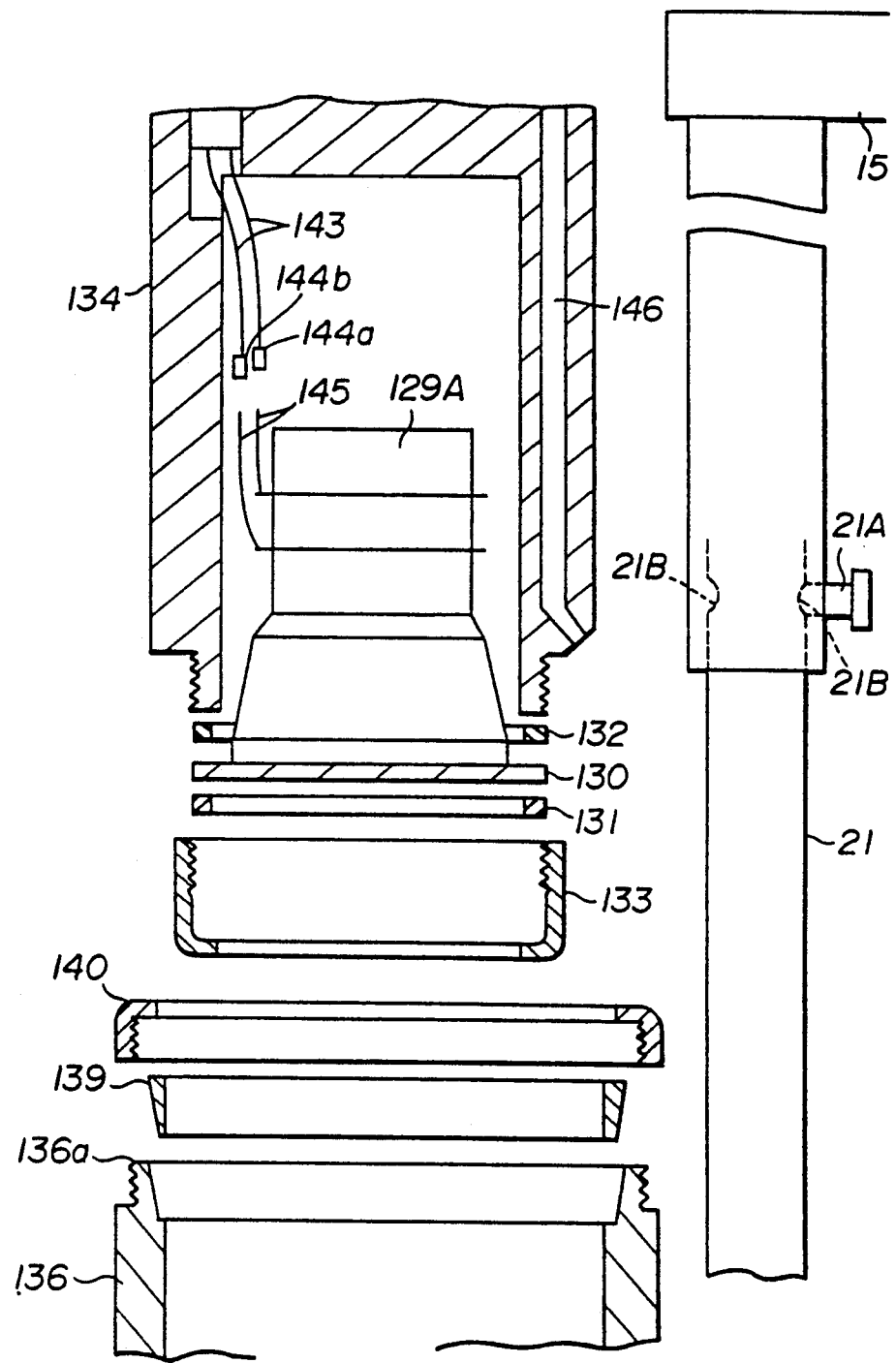

FIGS. 16 and 17 show the sixth embodiment of the present invention.

In this embodiment, the ultrasonic vibrator within the ultrasonic wave applicator is made easily replaceable.

That is to say, in this embodiment, the ultrasonic wave applicator 14 can be divided into a first part including at least the ultrasonic vibrator and a second part including the supporting part supported by said supporting member and provided with a vibrator removably fitting mechanism enabling the ultrasonic vibrator to be replaced.

FIG. 16 shows the ultrasonic wave applicator 14 in this embodiment.

An ultrasonic wave generating vibrator 129 (a bolted Langevin type ultrasonic vibrator is used here) is secured to a disc-like vibrating plate 130 which is fixed to an applicator body 134 by rubber rings 131 and 132 and a screw cap 133. An O-ring 135 is provided on the outer periphery of this applicator body 134 so as to keep water-tight the applicator body 134 and a cylindrical case 136 fitted to the applicator body 134. This case 136 is provided with a water bag 137 made of a film member of a soft resin so as to contain such ultrasonic wave transmitting agent 138 as water or ultrasonic wave gel to transmit ultrasonic waves to the human body 2.

The case 136 in the rear end part 136a is tapered on the inner periphery, is screw-threaded on the outer periphery and is fitted with a wedge ring 139 on the inside and a screw ring 140 on the outside. The wedge ring 139 is pressed by this screw ring 140 against the applicator body 134 so that the case 136 may be fixed to the applicator body 134. The applicator body 134 is fitted on the back surface with a connector 141 transmitting the output of the power amplifier 17 and a cock 142 injecting and discharging the ultrasonic wave transmitting agent 138. The connector 141 is connected at one end to the electric cable 16 transmitting the output of the power amplifier 17 and at the other end to leads 143 transmitting to the vibrator 129 the output from the power amplifier 17. These leads 143 are fitted with leads 145 pulled out the vibrator 129 and electrically connectable connectors 144a and 144b.

On the other hand, the applicator body 134 fitted with the cock 142 is provided with an injecting and discharging port 146 continuing into the water bag 137.

In the dissolving therapeutic apparatus of this embodiment, in the ultrasonic wave applicator 14 shown in FIG. 16, by loosening the screw ring 140 and screw cap 133, the vibrator 129 can be simply replaced with another vibrator 129A (See FIG. 17). Therefore, it is a feature of this embodiment that the vibrator 129 or 129A of a frequency adapted to the state in response to the state of the patient and the size of the stone, for example, the intrinsic vibration number of the stone or a frequency near to it can be simply fitted and used. In this embodiment, for example, a case 136 is fitted to the supporting member 21 and therefore it is also a feature of this embodiment that the oscillator 129 can be replaced while the case 136 is positioned as fixed to the supporting member 21 as it is.

The replacement of the vibrators 129 and 129A shall be explained in the following with reference to FIGS. 16 and 17.

In FIG. 16, first of all, the screw ring 140 is removed, the applicator body 134 is pulled out in the direction indicated by the arrow b on the case 136 side fixed to the supporting member 21, then the screw cap 133 is removed and the vibrator 129 is taken out together with the vibrating plate 130. Then, the connectors 144a and 144b are removed and the vibrator 129A (shown in FIG. 17) fitted with the vibrating plate 130 and having another frequency is fitted to the applicator body 134. In the fitting procedure, the leads 145 of the vibrator 129A are connected by the connectors 144a and 144b to the leads 143 extended out of the connector 141, the vibrating plate 130 is arranged so as to be held on both surfaces by the rubber rings 131 and 132 and is screwed to the applicator body 134 by the screw cap 133 and the vibrator 129A is fixed to the applicator body 134. Then, the applicator body 134 is fitted into the case 136 from above and a hose (not illustrated) connected at one end to a pump (not illustrated) is fitted to the cock 142 and the ultrasonic wave transmitting agent 138 is poured into the water bag 137 through the injecting and discharging port 146. In case air or the like is mixed into the ultrasonic wave transmitting agent 138 then, if the case is moved several times in the directions indicated by the arrows a and b, the air or the like will be discharged through the injecting and discharging port 146.

When the cock 142 is fastened, the wedge ring 139 is put into the case 136 on the inner perihery in the rear end part 136a and the screw ring 140 is fastened to the case 136 on the outer periphery in this outer end part 136, the wedge ring 139 will be pressed against the applicator body 134 and will be fixed to the applicator body 134. Then, the ultrasonic wave applicator 14 is again set on the body surface and the dissolving agent injection, ultrasonic wave radiation and dissolving agent suction are repeated.

When the stone 5 is completely dissolved, by operating the arm 15, the ultrasonic applicator 14 or observing ultrasonic wave probe 22 is removed from the human body 2, the catheter 6 is pulled out and the therapy ends.

According to this embodiment, by the simple operation of removing the wedge ring 139 and screw cap 133 while the applicator 14 (for example, on the case 136 side) is fitted to the supporting member 21, that is, while the applicator 14 is positioned as it is, only the parts (vibrator and vibrating plate) relating to the ultrasonic vibration can be replaced. Therefore, the vibrator of the vibration number emitting the ultrasonic waves adapted to accelerate the stone dissolving action directly in response to the size of the stone can be fitted, a therapeutic treatment can be made without requiring a positioning adjustment and a therapy high in the efficiency can be made.

The other formations, operations and effects are the same as in the first embodiment.

Figure 18:
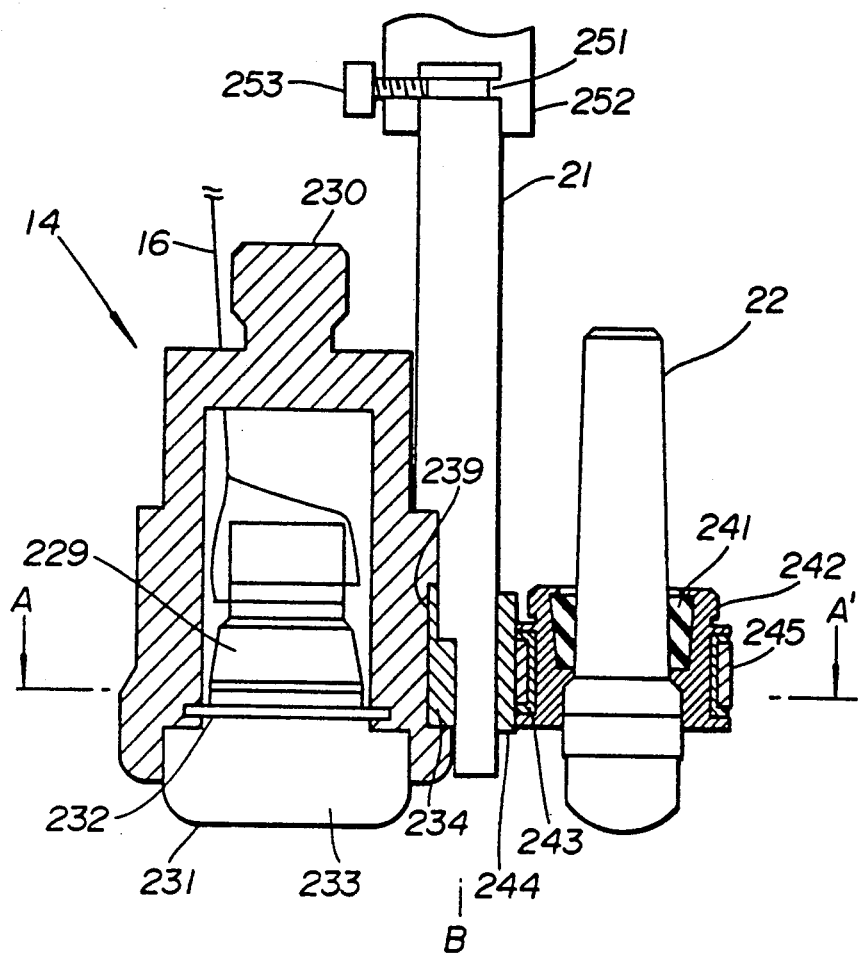
FIGS. 18 and 19 relate to the seventh embodiment of the present invention.
Figure 19:
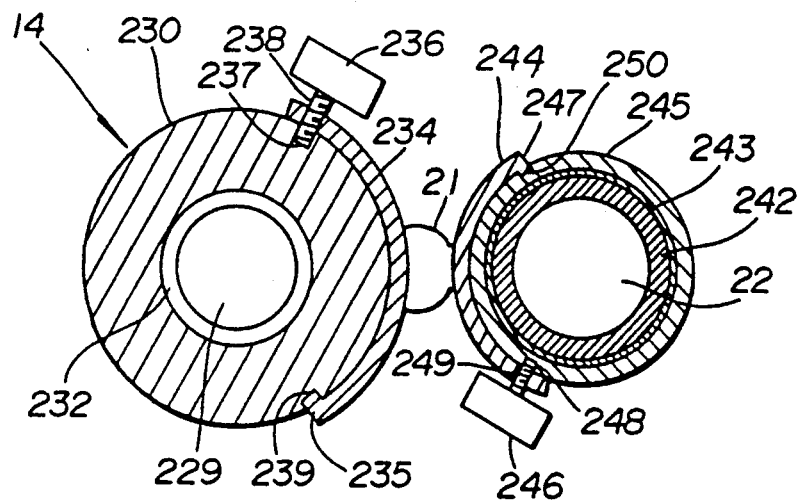

FIGS. 18 and 19 show the seventh embodiment of the present invention.

In this embodiment, the ultrasonic wave applicator 14 and ultrasonic wave probe 22 can be easily removably fitted and ca be positively fixed in accurate positions in fitting.

The formation of the essential part of this embodiment shall be explained with reference to FIGS. 18 and 19.

The ultrasonic wave applicator 14 comprises a housing 230 having an ultrasonic vibrator 229 within and a film 231 made of a soft resin or the like and provided in the lower end part of this housing 230. The vibrator 229 is secured on the front surface to an vibrating plate 232 by a bonding agent or the like and is held by the housing 230 through this vibrating plate 232. The space enclosed with the housing 230, film 231 and vibrating plate 232 is filled with such ultrasonic wave transmitting medium 233 as water. By the way, the vibrator 229 is electrically connected to the power amplifier 17 by a cable 16. The housing 230 is removably fixed and held by a connecting member 234 fixed to a supporting member 21 by such fastening member as a screw not illustrated.

As shown in FIG. 19, the housing 230 of the ultrasonic wave applicator 14 is cylindrical. On the other hand, the connecting member 234 is of an arcuate cross-section of a center angle less than 180 degrees with the axial direction of the ultrasonic wave applicator as a center or, in other words, is a part of a cylinder. The end surface (called a contact surface hereinafter) on the ultrasonic wave applicator 14 side of the connecting part 234 is of substantially the same radius of curvature as the radius of curvature of the outer peripheral surface of the housinng 230 of the ultrasonic wave applicator 14 and is to contact the outer peripheral surface of this housing 230. The contact surface is provided at one end in the peripheral direction with a projection 235 projecting in the center direction. On the other hand, the housing 230 is provided on the outer peripheral surface with a groove 239 engaging with the projection 235. Said connecting member 234 is provided near the other end in the peripheral direction with a through female screw part 238. The housing 230 is provided on the outer periphery with a female screw part 237 in a position corresponding to the female screw part 238 when said projection 235 and groove 239 are engaged with each other. When a screw 236 is screwed into the both female screw parts 237 and 238, the housing 230 will be fixed to the connecting member 234.

An observing ultrasonic probe 22 is arranged in a position (position different by 180 degrees) symmetrical with the ultrasonic wave applicator 14 with the center axis B of the supporting member 21 as a center and is held on the inner periphery of a cylindrical probe holder 242 through such elastic member 241 as a rubber. This probe holder 242 is connected to a ring 245 on the inner periphery through a sliding member 243. This ring member 245 is removably fixed and held by a connecting member 244 fixed to the supporting member 21 by such fastening member as a screw not illustrated. The method of fixing the ring 245 to said connecting member 244 is the same as the method of fixing the housing 230 of the ultrasonic wave applicator 14 to the connecting member 234. That is to say, the connecting member 244 is of an arcuate cross-section of a center angle less than 180 degrees with the axial direction of the ultrasonic wave probe 22 as a center or, in other words, is a part of a cylinder. The end surface (called a contact surface hereinafter) on the ring 245 side of the connecting member 244 is of a radius of curvature substantially the same as the radius of curvature of the outer peripheral surface of the ring 245 and is to contact the outer peripheral surface of this ring 245. The contact surface is provided in one end part in the peripheral direction with a projection 247 projecting in the center direction. On the other hand, the ring 245 is provided on the outer peripheral surface with a groove 250 engaging with the projection 247. The connecting member 244 is provided near the other end in the peripheral direction with a through female screw part 249. On the other hand, the ring 245 is provided on the outer periphery with a female screw part 248 in a position corresponding to the female screw part 249 when the projection 247 and the groove 250 are engaged with each other. When the screw 246 is screwed into the both female screw parts 248 and 249, the ring 245 will be fixed to the connecting member 244.

The scanning cross-section of the ultrasonic probe 22 is a plane including the center axis of the ultrasonic probe 22. The ultrasonic probe 22 is rotatable with respect to the ring 245 fixed to the connecting member 244 together with the probe holder 242.

By the way, a peripheral groove 251 is provided near the end (upper end) on the side opposite the part on which the connector member 234 and connecting part 244 are fixed of the supporting member 21 and this end is fitted within a connecting pipe 252 connected with the supporting arm 15 shown in FIG. 2. When a stopper 253 screwed in this connecting pipe 252 is engaged with the groove 251, the supporting member 21 will be rotatably fixed to the connecting pipe 252.

The respective operations of removably fitting the ultrasonic wave applicator 14 and ultrasonic probe 22, the observation by ultrasonic waves and the therapeutic procedure shall be explained in the following with reference to FIGS. 18 and 19.

First of all, in fitting the ultrasonic wave applicator 14, the groove 239 provided in the housing 230 is fitted to the projection 235 of the connecting member 234. The screw 236 held in the female screw part 238 of the connecting member 234 is rotated and is screwed and fastened into the female screw part 737 provided in the housing 230. On the contrary, in removing the ultrasonic wave applicator 14, the screw 236 is rotated in the reverse direction and is loosened so that the housing 230 may be removed from the connecting member 234.

In the same manner, in fitting the ultrasonic wave probe 22, the groove 250 provided in the ring 245 is fitted to the projection 247 of the connecting member 244 and the screw 246 held in the female screw part 249 of the connecting member 244 is rotated to be screwed and fastened in the female screw part 248. On the contrary, in removing the ultrasonic probe 22, if the screw 246 is rotated in the reverse direction to be loosened, the ultrasonic wave 22 will be able to be removed from the connecting member 244.

The operations of the observation and therapy by ultrasonic waves shall be explained in the following. First of all, with the ultrasonic probe 22 removed from the connecting member 234, the ultrasonic probe 22 is contacted at the tip with the human body 2 and the center axis direction and rotating direction are manually operated by the operator not illustrated. When the gallbladder 4 and stone 5 within the human body 2 are displayed on the center axis of the monitor 24, as described above, the ultrasonic probe 22 is fitted to the connecting member 244. Then, the arm 15 and supporting member 21 are operated and the ultrasonic probe 22 is rotated with the center axis as a center. Thereby, a scanning cross-section by the ultrasonic probe 22, that is, a cross-sectioned image will rotate with the center axis of the ultrasonic probe 22 as a center. By the way, when the ultrasonic probe 22 is rotated, the probe holder 242 to which this ultrasonic probe 22 is secured will rotate with respect to the ring 245 through the sliding member 243. By such operation, the operator can confirm whether the positions of the gallbladder 4 and stone 5 within the human body 2 are in the optimum positions on the image in the monitor 24. When they are in the optimum positions, the arm 15 and supporting member 21 are fixed and then, as described above, when the ultrasonic wave applicator 14 is fitted to the connecting member 234, the stopper 253 is loosened, the supporting member 21 is rotated by 180 degrees with the center axis of the supporting member 21 as a rotation center and the ultrasonic wave applicator 14 is set on the body surface. Here, if various kinds of the ultrasonic wave applicators 14 different in the frequency of the built-in ultrasonic vibrator 229 are prepared, the ultrasonic wave applicator 14 will be able to be selected in response to the object of the therapy.

As explained above, according to this embodiment, the ultrasonic wave applicator 14 and ultrasonic probe 22 can be removably fitted to the supporting member 21 and can be positively fixed in accurate positions by a simple operation in fitting, the dropping and displacement during the therapy can be prevented and a safe and effective therapy can be made.

Also, in this embodiment, in fitting the ultrasonic wave applicator 14 and ultrasonic probe 22, the projection and groove are engaged with each other so that they may be quickly and easily positioned. The housing 23 and O-ring 245 are gripped and fixed with the projections 235 and 247 engaged with the grooves and the screws 236 and 246 and therefore the ultrasonic wave applicator 14 and ultrasonic probe 22 can be positively fixed by one fixing means (screws).

According to this embodiment, by rotating the ultrasonic probe 22 with its center axis as a center, without changing the position relation of the ultrasonic probe and ultrasonic wave applicator 14, the scanning cross-section by the ultrasonic probe 22, that is, the cross-sectioned image can be rotated with the center axis of the ultrasonic probe 22 as a center. Therefore, in the case of searching an object to be treated with the ultrasonic probe 22 and fitting the ultrasonic wave applicator 14 to the treated object, the operatability is high.

The other formations, operations and effects are the same as in the first embodiment.

Figure 20:
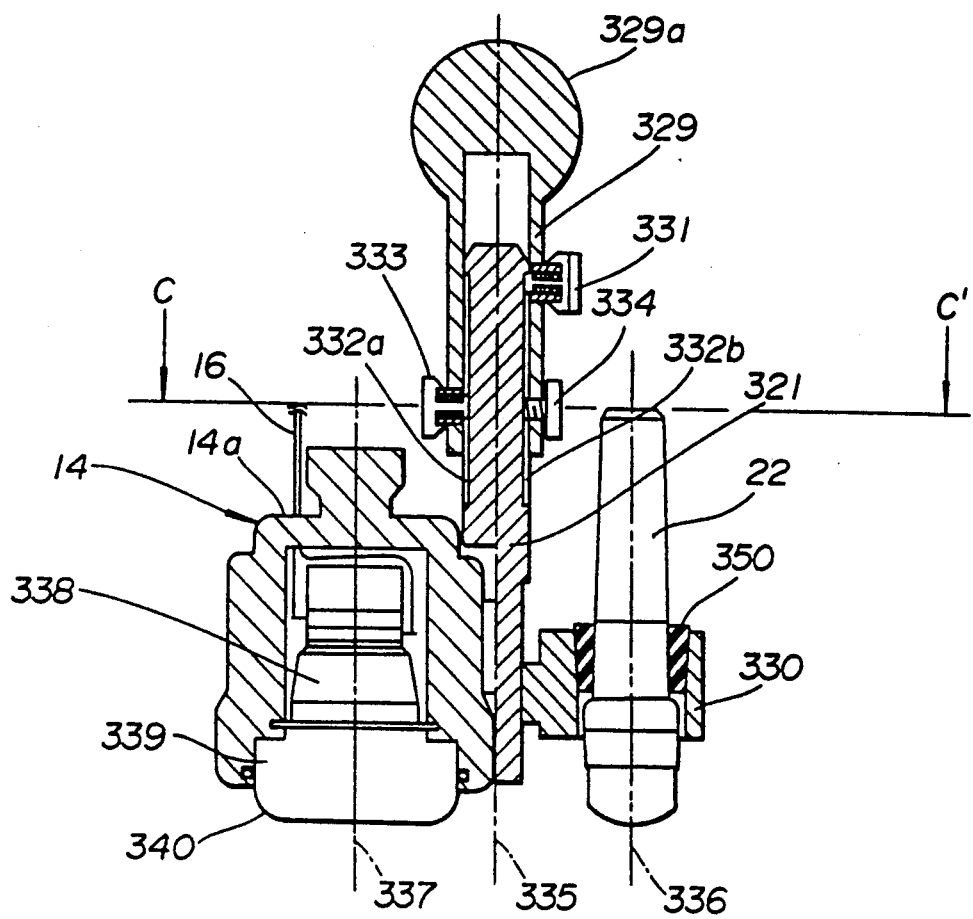
FIGS. 20 and 21 relate to the eighth embodiment of the present invention.
Figure 21:
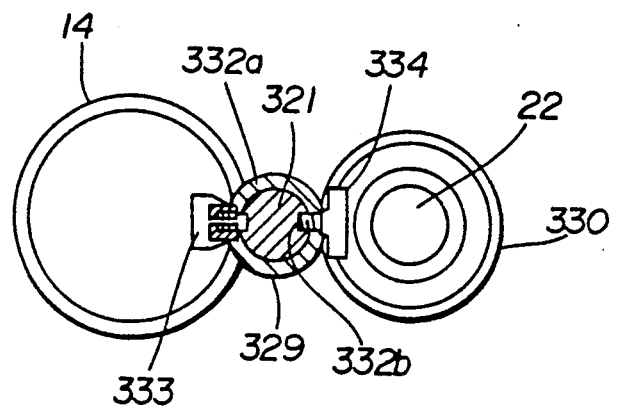

FIGS. 20 and 21 show the eighth embodiment of the present invention.

This embodiment is an example of an ultrasonic therapeutic apparatus wherein ultrasonic waves for accelerating the dissolution of a thickened mass can be radiated to the thickened mass in an accurate position relation with a simple formation and further the position relation of the sound field of ultrasonic waves generated by an ultrasonic vibrator for accelerating the dissolution of a thickened mass and the coagulation can be adjusted so that thickened mass dissolution accelerating ultrasonic waves may be radiated to the thickened mass at a high efficiency with a simple formation.

The means for positioning the ultrasonic wave applicator 14 and ultrasonic probe 22 shall be explained by using FIGS. 20 and 21.

Aa shown in FIG. 20, a sleeve 329 fitted to the tip of the supporting member 21 has a spherical part 329a at the upper end, is fitted angle-variably to the arm 15 through this spherical part 29a and is fitted rotatably with a rotor 321. That is to say, positioning grooves 332a and 332b are provided parallelly in the axial direction in positions symmetrical with respect to the center axis (in positions different by 180 degrees from each other) on the outer periphery of the rotor 321. A positioning pin 333 fitted to the sleeve 329 is engaged with one groove 332a and is energized in the direction of engaging with the groove 332a by a coil spring so that the rotor 321 may be positioned in the rotating direction by the engagement of the positioning pin 333 with the groove 332a. In the other groove 332b, a drop preventing pin 331 fitted to the sleeve 329 is engaged near the upper end and a fixing screw 334 screwed into the sleeve 329 is engaged in the position opposed to the positioning pin 333. The drop preventing pin 331 is energized in the direction of engaging with the groove 332b by a coil spring so that the rotor 321 may be prevented by this drop preventing pin 331 from dropping with respect to the sleeve 329. When the fixing screw 334 is fastened, the rotor 321 will be fixed with respect to the sleeve 329.

The ultrasonic probe 22 is fitted through an elastic member 350 to a supporting member 330 fixed to the rotor 321. The ultrasonic wave applicator 14 is fixed to said rotor 321 in the position symmetrical with said ultrasonic probe 22 with the center axis 335 of the rotor 321 as a center. The center axis 335 of the rotor 321, the visual field center axis 336 of the ultrasonic probe 22 and the ultrasonic wave radiation center axis 337 of the ultrasonic wave applicator 14 are parallel with one another and are arranged so that the distances of the axes 336 and 337 from the axis 335 may be respectively equal. The ultrasonic wave applicator 14 is provided with a housing 14a within which an ultrasonic vibrator 338 is fitted. The ultrasonic vibrator 338 is provided on the front surface with an elastic film 340 within which such ultrasonic wave transmitting medium 339 as water is kept.

The operation of the ultrasonic wave therapeutic apparatus of this embodiment shall be explained in the following.

First of all, the arm 15 and sleeve 329 are operated to search the vicinity of the gallbladder 4 with the ultrasonic probe 22. When the gallstone 5 is caught in the center within the display 24, the arm 15 and sleeve 329 are fixed so that the center axis 336 of the ultrasonic probe 22 and the gallstone 5 may be fixed on the same axis. Then, the fixing screw 334 of the rotor 321 is loosened, the positioning pin 333 is removed from the positioning groove 332 and the rotor 321 is rotated by 180 degrees until the positioning pin 333 fits in the positioning groove 332b and is fixed with the fixing screw 334 so that the gallstone 5 and the center axis 337 of the ultrasonic wave applicator 14 may be fixed on the same axis. Then, such numerical values as of the injected dissolving agent amount, ultrasonic wave radiating time and discharged dissolving agent amount are input by the inputting and controlling apparatus 20. By these numerical values, the apparatus is controlled by the controlling unit 19 and the dissolving therapy of the gallstone 5 is made. When the therapy ends, the rotor 321 is rotated by 180 degrees, the ultrasonic wave applicator 14 is replaced with the ultrasonic probe 22 and the gallstone 5 as dissolved is confirmed with the ultrasonic wave observing apparatus 23. Here, in case the gallstone 5 is recognized, the rotor 321 is rotated again by 180 degrees, the ultrasonic wave applicator 14 is set on the human body 2 and the operation is repeated. When the gallstone 5 is completely dissolved, the arm 15 is operated, the ultrasonic wave applicator 14 or ultrasonic probe 22 is removed from the human body 2, the catheter 6 is pulled out and the therapy ends.

Thus, according to this embodiment, with a small simple formation, one of the visual field center axis 336 which is the observed part by the ultrasonic probe 22 and the ultrasonic wave radiation center axis 337 which is the treated part by the ultrasonic wave applicator 14 (ultrasonic vibrator 338) can be selectively arranged and therefore the gallstone dissolution accelerating ultrasonic waves can be radiated to the gallstone 5 confirmed with the ultrasonic probe 22 in an accurate position relation.

The other formations, operations and effects are the same as in the first embodiment.

Figure 22:
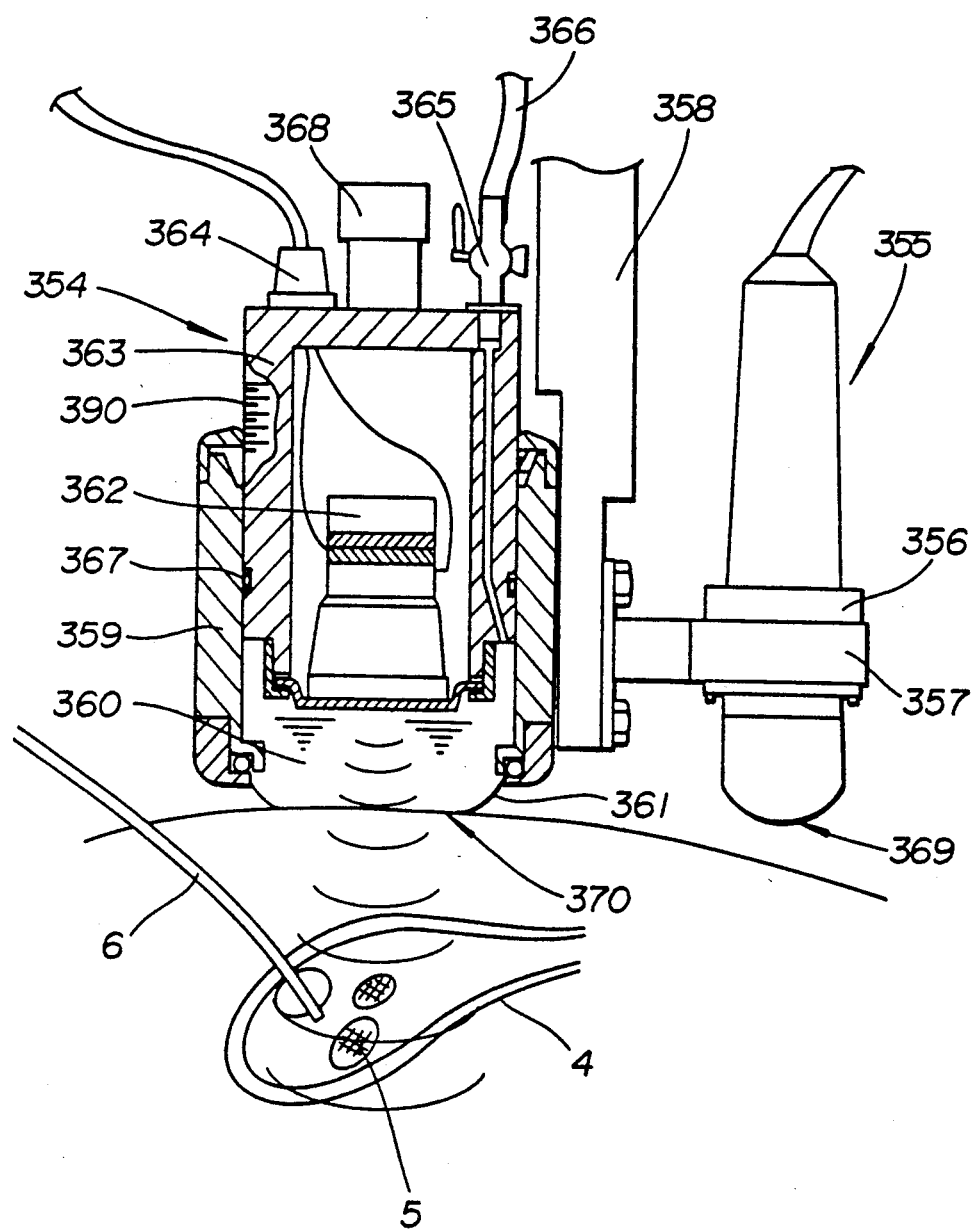
FIG. 22 is a partly sectioned side view showing the ultrasonic applicator and ultrasonic probe in the ninth embodiment of the present invention.

FIG. 22 shows the ninth embodiment of the present invention.

In this embodiment, an arm fixing member 358 is fitted to the arm 15. An ultrasonic wave applicator 354 is fixed to this arm fixing member 358. In a position symmetrical with the ultrasonic wave applicator 354 with the center axis of the arm fixing member 358 as a center, an ultrasonic probe 355 is rotatably fixed through an ultrasonic probe fixing member 357 and ultrasonic probe rotating and fixing member 356.

The ultrasonic applicator 354 is provided with an outer cylinder part 359 fixed to the arm fixing member 358 and an inner Cylinder part 363 slidably fitted within this outer cylinder part 359. Said outer cylinder part 359 is provided at the lower end with a pouch 361 made, for example, of a latex. This pouch 361 and the outer cylinder part 359 are filled with such ultrasonic wave transmitting medium 360 as, for example, deaerated water. An ultrasonic vibrator (here a bolted Langevin type ultrasonic vibrator) 362 is fitted within the inner cylinder part 363 which is kept water-tight inside and outside. The inner cylinder part 363 is provided at the upper end with a connector 364 for connecting the power amplifier 17 and ultrasonic vibrator 362 with each other so that the current from the power amplifier 17 may be fed to the ultrasonic vibrator 362 through this connector 364. Also, the inner cylinder part 363 is provided at the upper end with a cock 365 for injecting the ultrasonic wave transmitting medium 360 into the outer cylinder part 359 through a liquid feeding path within the side wall of this inner cylinder part 363. This cock 365 is connected through a tube 366 to a tank not illustrated storing the ultrasonic wave transmitting medium. The inner cylinder part 363 is provided at the upper end with a grip 368 for vertically moving this inner cylinder part 363. An O-ring 367 is provided between the inner cylinder part 363 and outer cylinder part 359 to keep them water-tight between them.

The inner cylinder part 363 is provided on the outer periphery with a scale 390 so that the position relation with the outer cylinder part 359 may be known.

By the way, the arm fixing member 358 consists of the sleeve 329 and rotor 321, for example, in the eighth embodiment so that, by rotating it by 180 degrees, the same as in the eighth embodiment, the ultrasonic probe 355 and ultrasonic wave applicator 354 may be selectively positioned on the axis passing through the gallstone 5. When positioned on the axis passing through the gallstone 5, the position of the surface (reference plane) 369 of said ultrasonic probe 355 and the position of the surface (reference plane) of the ultrasonic wave applicator 354, that is, the surface 370 of the pouch 361 will coincide with each other.

The other formations are the same as in the eighth embodiment.

The operation of this embodiment shall be explained in the following.

In the therapy, first of all, the position of the gallstone 5 is confirmed with the ultrasonic probe 355. Then, the ultrasonic wave applicator 354 is moved to the position observed with the ultrasonic wave probe 355. At this time, the position of the surface 370 of the pouch 361 and the position of the surface 369 of the ultrasonic probe 355 will coincide with each other. The distance from the body surface to the gallstone 5 can be measured with the ultrasonic probe 355. That is to say, the distance from the surface 370 of the pouch 361 to the gallstone 5 can be determined. Therefore, if the distance from the body surface, that is, the surface 370 of the pouch 361 to the ultrasonic wave radiating plane of the ultrasonic vibrator 362 of the ultrasonic wave applicator 354 is known, the distance from the ultrasonic wave radiating plane to the gallstone 5 will be known. The distance from the surface 370 of the pouch 361 to the ultrasonic wave radiating plane of the ultrasonic vibrator 362 of the ultrasonic wave applicator 354 can be adjusted by vertically moving the inner cylinder part 363 with respect to the outer cylinder part 359 by holding the grip 368 and can be known by the scale 390 provided on the inner cylinder part 654. Thus, by vertically moving the inner cylinder part 363 with respect to the outer cylinder part 359, the position relation of the ultrasonic wave oscillator 342 and the gallstone 5 can be adjusted so as to be of an ultrasonic wave radiating state or sound field adapted to the therapy.

Thus, according to this embodiment, the ultrasonic probe 355 and the outer cylinder part 363 of the ultrasonic wave applicator 354 are fixed so that the position relation of the respective reference planes may be clear, the position of the gallstone 5 is observed with the ultrasonic probe 355, then the ultrasonic wave applicator 354 is arranged on the axis passing through the gallstone 5 and further the inner cylinder part 363 to which the ultrasonic vibrator 362 is fixed is moved with respect to the outer cylinder part 359 so that the therapy may be made in the most efficient therapeutic ultrasonic wave radiation with a simple formation and a compact mechanism.

The other operations and effects are the same as in the eighth embodiment.

Figure 23:
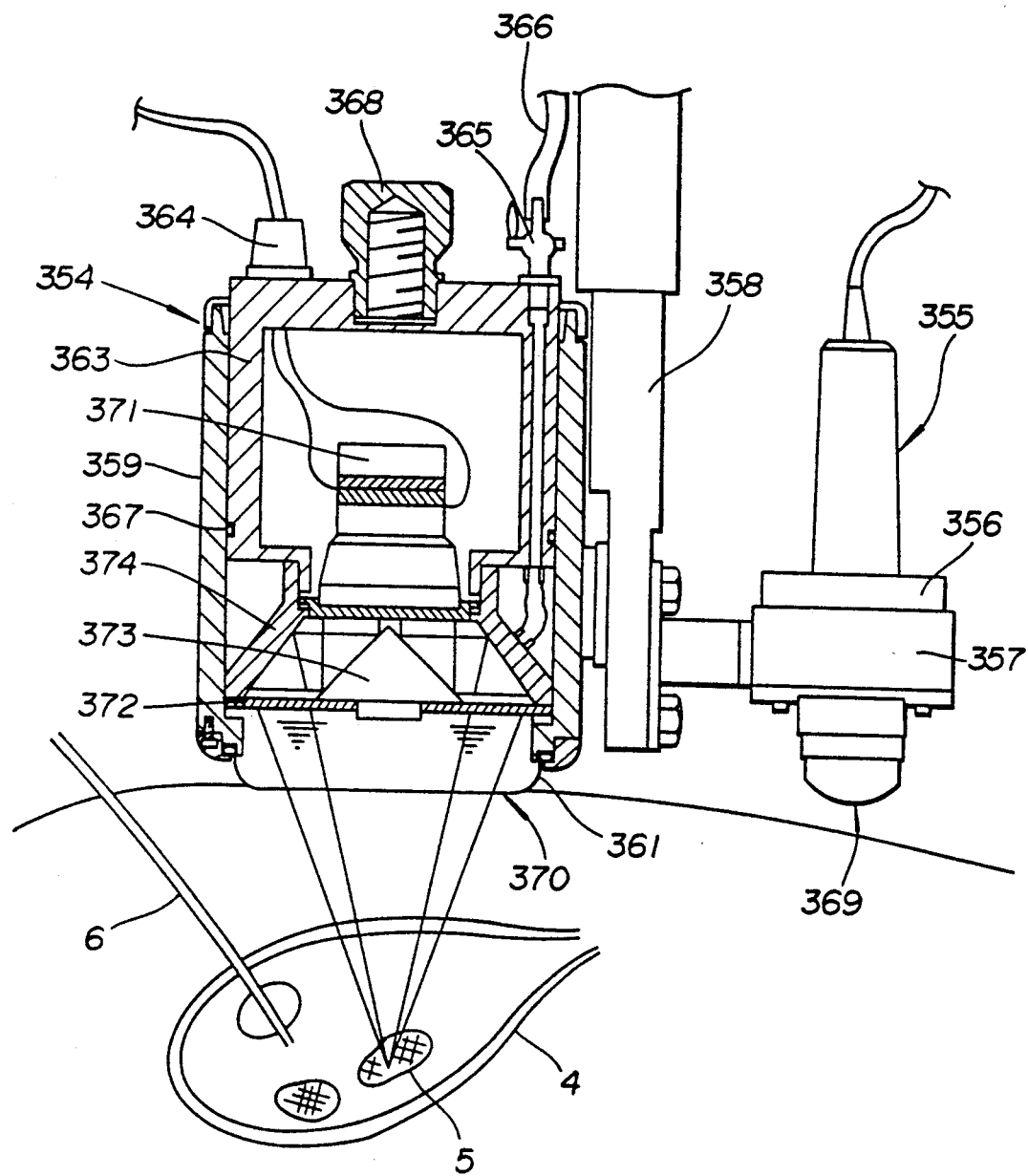
FIG. 23 is a partly sectioned side view showing the ultrasonic applicator and ultrasonic probe in the tenth embodiment of the present invention.

FIG. 23 shows the tenth embodiment of the present invention.

In this embodiment, an ultrasonic vibrator 371 is provided within an inner cylinder part 363 and a reflector 374 having a parabolic surface is fixed to the inner cylinder part 363 at the lower end. A conical cone 373 is provided in front of the ultrasonic wave radiating plane of the ultrasonic vibrator 371 and is fixed to the reflector 373 at the lower end by a supporting member 372.

In this embodiment, the ultrasonic waves emitted from the ultrasonic vibrator 371 are reflected by the cone 373 and are further reflected and condensed by the reflector 374.

According to this embodiment, by moving the inner cylinder part 363 with respect to the outer cylinder part 359, the therapeutic ultrasonic wave condensing region can be made to coincide with the gallstone 5 and a further effective therapy can be made.

The other formations, operations and effects are the same as in the eighth or ninth embodiment.

Figure 24:
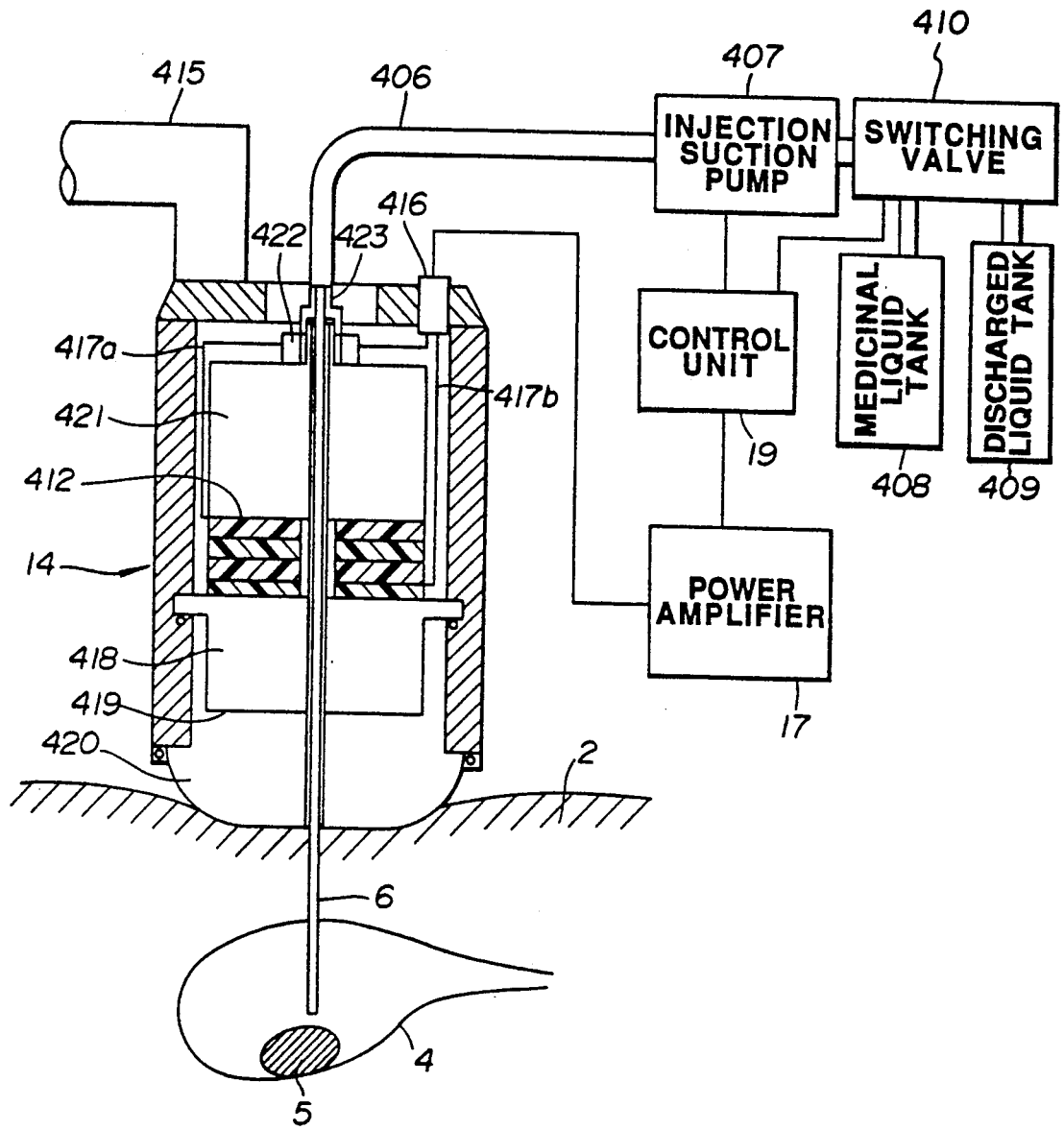
FIGS. 24 and 25 relate to the 11th embodiment of the present invention.
Figure 25:
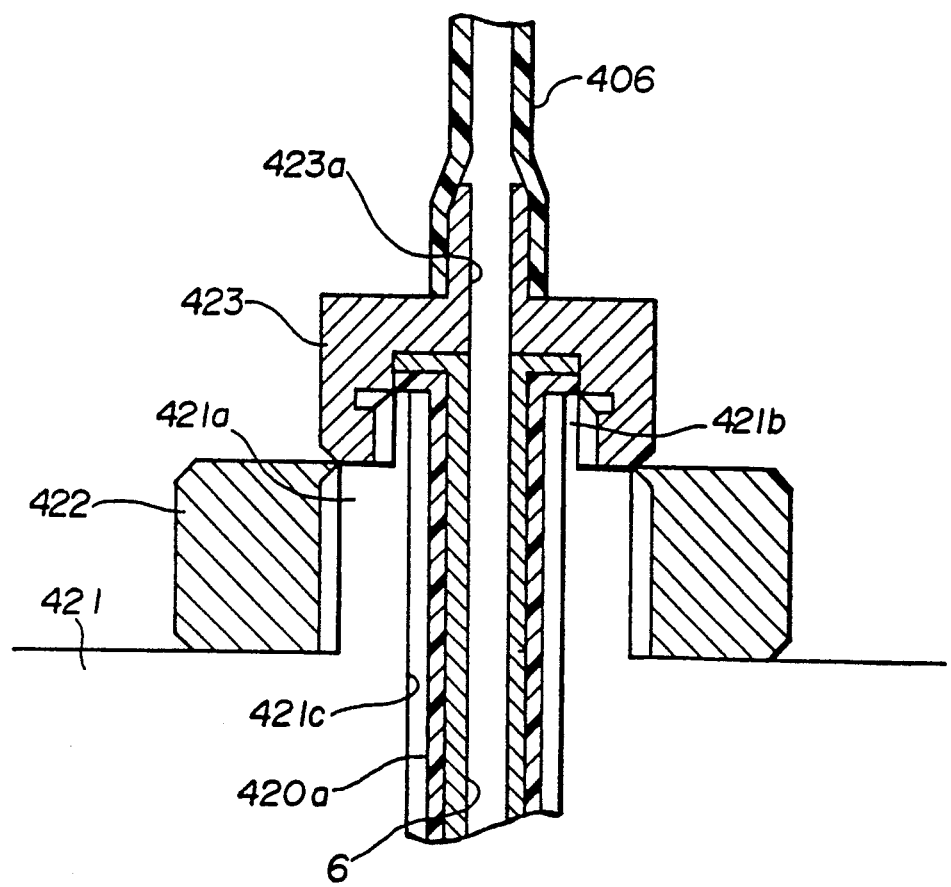

FIGS. 24 and 25 show the 11th embodiment of the present invention. In this embodiment, the ultrasonic wave energy from the ultrasonic wave applicator can be efficiently given to the treated part.

As shown in FIG. 24, the dissolving therapeutic apparatus of this embodiment is provided with a catheter 6 formed of a hard, for example, metal pipe which is dermally inserted through such treated part of the human body 2 as, for example, the gallbladder 4 to inject a dissolving agent for dissolving such coagulation as, for example, the stone 5 and to suck the fluid from the gallbladder 4, an injection and suction pump communicating with said catheter 6 through a tube 406 to inject said dissolving agent or to suck the fluid and a switching valve 410 for connecting a medicinal liquid tank 408 containing the dissolving agent or a discharged liquid tank 409 storing the fluid sucked from the gallbladder 4. Said injection and suction pump 407 and switching valve 410 are controlled by a controlling unit 19 so that the injection of the medicinal liquid into the gallbladder 4 or the suction of the fluid from the gallbladder may be controlled. An ultrasonic wave applicator 14 to be contacted with the body surface of the human body 2 has an ultrasonic vibrator 412 radiating such oscillated waves as, for example, ultrasonic waves to the gallbladder 5. This ultrasonic vibrator 412 is connected to a power amplifier 17. The ultrasonic wave applicator 14 is supported so as to contact the body surface of the human body by an applicator supporting part 415.

The power amplifier 17 is connected to said ultrasonic wave applicator 14 by a connector 416 and is connected to the ultrasonic vibratorr 412 by signal lines 417a and 417b connected to this connector 416.

The ultrasonic vibrator 412 is, for example, a bolted Langevin type ultrasonic vibrator. A vibrating member 418 is arranged on the body surface side of the living body 2 of said ultrasonic vibrator 412 and a water bag 420 filled with such ultrasonic wave transmitting liquid as water is arranged on the radiating surface 419 on the body surface side of said living body 2 of this vibrating member 418. A back mass 421 is arranged on the surface opposite the body surface of said living body of said ultrasonic vibrator 412 and is supported on the outer fitting surface of the ultrasonic wave applicator 14 by a nut 422 and bolt 423.

As described later, a hole is formed through the ultrasonic vibrator 412, vibrating member 418 and back mass 421 and the catheter 6 is to be inserted through this hole.

The essential part relating to the back mass 421, nut 422 and bolt 423 shall be explained by using FIG. 25.

A screw part 421a with which the nut 422 is screwed and a scarew part 421b with which the bolt 423 is screwed are formed on the back mass 421 and a hole 421c is made substantially in the center position of these screw parts 421a and 421b.

A film 420a which is an outer peripheral member of the water bag 420 and said catheter 6 are inserted through the hole 421c, are folded back at the ends at the upper end of the screw part 421b and are fixed to the back mass 421 by the engagement of the bolt 423 with the upper end surface of the screw part 421b.

The bolt 423 projects on the surface opposite the surface screwed with the screw part 421b. Further, a hole 423a is formed substantially in the center position of the bolt 423 so as to communicate with the catheter 6. The tube 406 is connected to the above described projecting part so as to communicate with the catheter 6.

Said controlling unit 19 controls the switching valve 410 to connect the medicinal liquid tank 408 and the injection-suction pump 407 with each other so that the injection-suction pump 407 may inject the dissolving agent within the medicinal liquid tank 408 into the gallbladder 4 through said switching valve 10, tube 406, bolt 423 and catheter 6 and controls the switching valve 410 to connect the discharged liquid tank 409 and the injection-suction pump 407 with each other so that the injection-suction pump 407 may be controlled to suck the fluid from said gallbladder 4 into the discharged liquid tank 9 through the catheter 6, bolt 423, tube 406 and switching valve 410.

The other formations are the same as in the first embodiment.

The operation of the thus formed dissolving therapeutic apparatus shall be explained. In the ultrasonic wave radiating period in the sequence of the dissolving therapy of the first embodiment, the driving signal output from the oscillator 18 and through the output adjusting circuit 43 within the controlling unit 19 and the power amplifier 17 is fed to the ultrasonic vibrator 412 through the connector 416 and signal lines 417a and 417b and thereby the ultrasonic vibrator 412 vibrates.

The vibration of the ultrasonic vibrator 412 is transmitted to the vibrating member 418 and is transmitted from the radiating surface 419 of the vibrating member 418 to the gallbladder 4 through the water bag 420 and the body surface of the human body 2.

Further, the vibration of the ultrasonic vibrator 412 is transmitted to the back mass 421, the back mass 421 vibrates and thereby the catheter 6 fixed to the back mass 421 vibrates on the base side.

The vibration of the catheter 6 on the base side is transmitted to the tip part of the catheter 6 positioned within the gallbladder 4.

Thereby, vibrating waves by the vibration of the catheter 6 are generated near the tip part of the catheter 6 and reach the gallstone 5 and the destruction of the gallstone 5 is accelerated.

By the way, the catheter 6 may be contacted with the gallstone 5 so that the vibration of the catheter 6 may be directly transmitted to accelerate the destruction of the gallstone 5.

In case it is not necessary to transmit the vibration to the catheter 6, said catheter 6 may be used as formed of a soft, for example, synthetic resin.

Thus, according to this embodiment, there is an effect that the vibrating waves radiated to the surface opposite the living body of the ultrasonic vibrator which have not been used heretofore can be effectively used.

The other operations and effects are the same as in the first embodiment.

It is apparent that, in this invention, working modes different in a wide range can be formed on the basis of this invention without deviating from the spirit and scope of the invention. This invention is not restricted by its specific working modes except being limited by the appended claims.

What is claimed is:

1. A method of dissolving a thickened mass within a living body and discharging it out of the living body, comprising the steps of:
   injecting into said living body a medicinal liquid for dissolving said thickened mass within said living body;
   leaving with said living body for a predetermined time said medicinal liquid injected by said injecting step in order to dissolve said thickened mass with said medicinal liquid;
   discharging out of the living body substantially all of the fluid within said living body containing said thickened mass dissolved by said medicinal liquid in said leaving step and said medicinal liquid; and
   repeating a series of steps including at least said injecting step, leaving step and discharging step, wherein said medicinal liquid is replaced with fresh medicinal liquid before said medicinal liquid is saturated with said thickened mass.

2. A method according to claim 1 further comprising a step of setting the time for leaving said medicinal liquid within said living body in said leaving step on the basis of dissolving conditions including the size of said thickened mass and the kind of said medicinal liquid.

3. A dissolving therapeutic apparatus for dissolving a thickened mass within a living body, comprising:
   an injecting means for injecting into said living body a medicinal liquid for dissolving said thickened mass within said living body;
   a sucking means for sucking the fluid within said living body containing said medicinal solution and discharging it out of the living body; and
   a controlling means for controlling said injecting means and sucking means so as to make the respective steps of injecting said medicinal liquid into said living body by operating said injecting means, leaving said injecting medicinal liquid within said living body for a predetermined time and discharging out of the living body said fluid within the living body containing said thickened mass dissolved by said left medicinal liquid and said medicinal liquid by operating said sucking means, wherein said medicinal liquid is replaced with fresh medicinal liquid before said medicinal liquid is saturated with said thickened mass.

4. An apparatus according to claim 3 wherein:
   said injecting means comprises a liquid tank storing said medicinal liquid not yet used, an injecting conduit means for leading said medicinal liquid within said liquid tank into said living body and an injection pump generating an injection pressure for injecting said medicinal solution into said living body through said injecting conduit means; and
   said sucking means comprises a discharged liquid tank storing said discharged fluid, a sucking conduit means for leading said fluid within the living body into said discharged liquid tank and a suction pump generating a suction pressure for sucking said fluid through said sucking conduit means and discharging it into said discharged liquid tank.

5. An apparatus according to claim 4 further comprising a single catheter having said injecting conduit means and said sucking conduit means built-in.

6. An apparatus according to claim 3 wherein said injecting means includes a liquid tank storing said medicinal liquid not yet used, said sucking means includes a discharged liquid tank storing said discharged fluid and said injecting means and sucking means include a single conduit means for leading said medicinal liquid within said liquid tank into said living body and for leading said fluid within the living body into said discharged liquid tank and a single pump alternately generating an injection pressure for injecting said medicinal liquid into said living body through said conduit means and a suction pressure for sucking said fluid through said conduit means and discharging it into said discharged liquid tank.

7. An apparatus according to claim 3 wherein said controlling means includes a setting means for setting the injected amount and sucked amount of said medicinal liquid.

8. An apparatus according to claim 7 wherein the injecting speed of said injecting means is constant and said setting means sets said injected amount by the injecting time by said injecting means.

9. An apparatus according to claim 3 wherein said controlling means includes a setting means for setting the time for leaving said medicinal liquid within said living body on the basis of dissolving conditions including the size of said thickened mass and the kind of said medicinal liquid.

10. An apparatus according to claim 3 wherein said controlling means includes a setting means for setting the number of repetitions of the injection, leaving and suction.

11. An apparatus according to claim 3 wherein said controlling means includes a setting means for setting the respective times for the injection, leaving and suction and the number of repetitions of the injection, leaving and suction and a means for operating all the therapeutic time on the basis of the conditions set by said setting means.

12. An apparatus according to claim 3 further comprising a vibrating wave generating means controlled by said controlling means and generating vibrating waves toward said thickened mass.

13. An apparatus according to claim 12 wherein said controlling means operates said vibrating wave generating means at least in said leaving step.

14. An apparatus according to claim 12 wherein said vibrating wave generating means includes an ultrasonic wave applicator having an ultrasonic vibrator built-in and applied to the body wall.

15. An apparatus according to claim 3 further comprising a pressure detecting means for detecting that the pressure of said medicinal liquid injecting part has become a predetermined upper limit pressure.

16. An apparatus according to claim 15 wherein said controlling means will forcibly stop said injecting means when said pressure detecting means detects that the pressure of said injecting part has become said upper limit pressure in said injecting step.

17. An apparatus according to claim 15 wherein said pressure detecting means includes an offset adjusting means for adjusting the offset of the detected output.

18. An apparatus according to claim 15 wherein said controlling means includes a forcibly operating means for forcibly operating said sucking means when said pressure detecting means detects that the pressure of said injecting part has become said upper limit pressure in said leaving step.

19. An apparatus according to claim 18 wherein said controlling means includes a correcting means for correcting the sucked amount in said sucking step by subtracting the sucked amount part by said forcibly operating means.

20. An apparatus according to claim 15 further comprising a catheter to be arranged at the forward end within the living body and at the base end outside the living body, said injecting means including an injecting path for leading said medicinal liquid into said living body, said sucking means including a sucking path for leading said fluid within said living body into said discharged liquid tank, said catheter having said injecting path and sucking path built-in and said pressure detecting means including a pressure conduit provided within said catheter, opening at one end near said forward end of said catheter and having the other end on the side opposite said one end and a pressure sensor to which said pressure conduit is connected at said other end.

21. An apparatus according to claim 20 wherein said pressure detecting means further includes an adjusting means for adjusting the arranged height of said pressure sensor.

22. An apparatus according to claim 3 wherein said controlling means sucks the same amount of the fluid as the amount of the medicinal liquid injected in said injecting step.

23. An operation setting apparatus to be used for dissolving therapeutic apparatus wherein a medicinal liquid for dissolving a thickened mass within a living body is injected into said living body, said injected medicinal liquid is held within said living body and the fluid within the living body containing said thickened mass dissolved by said medicinal liquid and said medicinal liquid is discharged out of the living body, comprising:
 a holding time setting means for optionally setting the time for holding within said living body said medicinal liquid injected into said living body; and
 a repeating number setting means for optionally setting the number of repetitions of the three of injecting, holding and discharging steps as one unit, wherein said medicinal liquid is replaced with fresh medicinal liquid before said medicinal liquid is saturated with said thickened mass.

24. An apparatus according to claim 23 further comprising an injecting time setting means for optionally setting the medicinal liquid injecting time to determine the injected amount of the medicinal liquid in said injecting step.

25. An apparatus according to claim 24 wherein said discharging step operating time is automatically set so as to be the same as said medicinal liquid injecting time.

26. An apparatus according to claim 23 further comprising an operating means for operating all the operating time on the basis of the operating manner set by said holding time setting means and said repeating number setting means and a displaying means for displaying the operating result of said operating means.

27. An apparatus according to claim 26 wherein said displaying means displays the elapsing time from the operation starting time to said apparatus together with said all operating time.

28. A dissolving therapeutic apparatus for dissolving a thickened mass within a living body, comprising:
an injecting means for injecting into said living body a medicinal liquid for dissolving said thickened mass within said living body;
a sucking means for sucking the fluid within said living body containing said medicinal liquid and discharging it out of the living body;
a pressure detecting means for detecting the pressure of the injecting part of said medicinal liquid injected by said injecting means;
a controlling means for controlling said injecting means and sucking means;
a setting means operatively connected to said controlling means and for setting in advance the time table of the operations of said injecting means and sucking means; and
said controlling means having a time controlling mode controlling said injecting means and sucking means according to said time table an a pressure controlling mode wherein, when said pressure detecting means detects that the pressure of said injecting part has exceeded a predetermined pressure, apart from the control by said time controlling mode, at least one of said injecting means and sucking means will be controlled and the pressure of said injecting part will be adjusted so that the pressure detected by said pressure detecting means may be below said predetermined pressure, wherein said medicinal liquid is replaced with fresh medicinal liquid before said medicinal liquid is saturated with said thickened mass.

29. An apparatus according to claim 28 wherein said controlling means will return to said time controlling mode when the pressure detected by said pressure detecting means becomes below said predetermined pressure in said pressure controlling mode.

30. An apparatus according to claim 28 wherein said controlling means controls at least one of said injecting means and sucking means by changing said time table in said pressure controlling mode.

31. An apparatus according to claim 30 wherein said controlling means, in said time controlling mode, repeats as one unit the three of the injecting step by said injecting means, the leaving step of leaving within said living body said injected medicinal liquid and the sucking step by said sucking means and, in said pressure controlling mode, changes said time table in said one unit.

32. An apparatus according to claim 31 wherein said time table is changed without changing all time of said one unit.

33. An apparatus according to claim 28 wherein said pressure controlling mode includes that, in case the pressure detected by said pressure detecting means exceeds said predetermined pressure during the operation of said injecting means in said time controlling mode, even within the injecting time set by said setting means, the injecting operation will be stopped and the next sucking time will be changed to be the same time as the injecting time until the injecting operation is stopped.

34. An apparatus according to claim 28 wherein said controlling means includes that, in said time controlling mode, the three of the injecting step by said injecting means, the leaving step of leaving within said living body said injected medicinal liquid and the sucking step by said sucking means are repeated in a time set in advance and, in said pressure controlling mode, in case the pressure detected by said pressure detecting means exceeds said predetermined pressure in said leaving step, even within the set leaving time, said sucking means will be urgently operated so that said detected pressure may be below said predetermined pressure, the sucked amount by said urgent operation will be determined and the sucking time in the next sucking step will be changed to be the time obtained by subtracting the time corresponding to said sucked amount by said urgent operation from the set sucking time.

35. A dissolving therapeutic apparatus for dissolving a coagulation within a living body, comprising:
a catheter for injecting into said living body a medicinal liquid for dissolving said coagulation within said living body, sucking the fluid within said living body containing said medicinal liquid and discharging said fluid out of the living body;
a vibrating wave observing apparatus for observing the ultrasonic wave image of the observed part within said living body;
a vibrating wave generating apparatus for applying vibrating waves to accelerate the dissolution of the coagulation to the treated part within said living body; and
a supporting apparatus for supporting said ultrasonic wave observing apparatus and vibrating wave generating apparatus, said supporting apparatus including a moving means for moving said observing apparatus and vibrating wave generating apparatus so as to selectively arrange said observing part of said observing apparatus and said treating part of said vibrating wave generating apparatus in any desired part of said living body.

36. An apparatus according to claim 35 wherein said supporting apparatus further includes a supporting member fixing said observing apparatus and said vibrating wave generating apparatus and rotatable with the position at equal distances from the fixing position of said observing apparatus and the fixing position of said vibrating wave generating apparatus as a center and said moving means is to rotate said supporting member.

37. A dissolving therapeutic apparatus for dissolving a thickened mass within a living body, comprising:
an injecting means for injecting into said living body a medicinal liquid for dissolving said thickened mass within said living body;
a sucking means for sucking the fluid within said living body containing said medicinal liquid and discharging said fluid out of the living body; and
a controlling means for controlling said injecting means and sucking means so as to make an injecting step of injecting said medicinal liquid into said living body by operating said injecting means and a sucking step of discharging out of the living body said fluid within the living body containing said coagulation dissolved by said medicinal liquid and said medicinal liquid by operating said sucking means;
said controlling means controlling said injecting means and sucking means so as to provide a medicinal liquid movement pausing period for radiating vibrating waves toward said thickened mass between said injecting step and sucking step, wherein said medicinal liquid is replaced with fresh medicinal liquid before said medicinal liquid is saturated with said thickened mass.

38. An apparatus according to claim 37 which is an apparatus for dissolving a gallstone as said coagulation and in which said medicinal liquid is to dissolve said gallstone.

39. A dissolving therapeutic apparatus for dissolving a gallstone within a gallbladder, comprising:
an injecting means for injecting into said gallbladder a medicinal liquid for dissolving said gallstone within said gallbladder;
a sucking means for sucking the fluid within said gallbladder containing said medicinal liquid and discharging said fluid; and
a controlling means for controlling said injecting means and sucking means so as to repeat as one unit at least three steps including an injecting step of injecting said medicinal liquid into said gallbladder by operating said injecting means, a leaving step of leaving said medicinal liquid within said gallbladder by stopping the operation of said injecting means and making the operation of dissolving said gallstone with said left medicinal liquid and a sucking step of discharging out of the gallbladder the fluid within said gallbladder containing said medicinal liquid having ended said dissolving operation by operating said sucking means;
said controlling means controlling said injecting means and sucking means so as to provide a pausing step for sucking the increased part of said fluid by the gall having flowed into said gallbladder, as required, by operating said sucking means after said sucking step, wherein said medicinal liquid is replaced with fresh medicinal liquid before said medicinal liquid is saturated with said thickened mass.

40. An apparatus according to claim 39 further comprising a pressure detecting means for detecting the pressure within said gallbladder, said controlling means operating said sucking means in response to the detected output of said pressure detecting means in said pausing step.

41. An apparatus according to claim 39 wherein said controlling means provides said pausing step at intervals of several repetitions of said unit.

* * * * *